(12) United States Patent
Vink et al.

(10) Patent No.: US 8,759,095 B2
(45) Date of Patent: Jun. 24, 2014

(54) DIAGNOSTIC AND THERAPEUTIC TOOLS FOR DISEASES ALTERING VASCULAR FUNCTION

(75) Inventors: Hans Vink, Schimmert (NL); Erik Sjoerd Gerard Stroes, Den Dolder (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 391 days.

(21) Appl. No.: 12/734,876

(22) PCT Filed: Dec. 1, 2008

(86) PCT No.: PCT/EP2008/066524
§ 371 (c)(1),
(2), (4) Date: Jul. 30, 2010

(87) PCT Pub. No.: WO2009/068685
PCT Pub. Date: Jun. 4, 2009

(65) Prior Publication Data
US 2010/0304424 A1     Dec. 2, 2010

(30) Foreign Application Priority Data
Nov. 30, 2007   (EP) .................................... 07122043

(51) Int. Cl.
*C12N 5/00*    (2006.01)
*C12N 5/071*   (2010.01)
*C12Q 1/00*    (2006.01)
*C12Q 1/02*    (2006.01)

(52) U.S. Cl.
USPC ................. 435/366; 435/4; 435/29; 435/325

(58) Field of Classification Search
None
See application file for complete search history.

(56) References Cited

FOREIGN PATENT DOCUMENTS

| | | |
|---|---|---|
| JP | A 7-308312 | 11/1995 |
| JP | A 2003-510112 | 3/2003 |
| JP | A 2007-054483 | 3/2007 |
| JP | A 2007-536974 | 12/2007 |
| WO | WO 2005/023111 | 3/2005 |
| WO | WO 2007/075388 A | 7/2007 |
| WO | WO 2009/068685 A1 | 6/2009 |

OTHER PUBLICATIONS

Huntsberger, in Elements of Statistical Inference, 2nd ed., Allyn and Bacon, 1967, Boston, MA, pp. 168-169.*
Nieuwdorp et al.. Measuring endothelial glycocalyx dimensions in humans: a potential novel tool to monitor vascular vulnerability. Journal of Applied Physiology. Mar. 2008. pp. 845-852, vol. 104, No. 3.
Nieuwdorp et al.. Loss of endothelial glycocalyx during acute hyperglycemia coincides with endothelial dysfunction and coagulation activation in vivo. Diabetes. Feb. 2006, pp. 480-486. vol. 55, No. 2.
Nieuwdorp et al., LPS-Induced systemic inflammation results in rapid loss of endothelial glycocalyx in humans, Circulation. Oct. 2005, p. U162. vol. 112. No. 17, American Heart Association. Dallas, Texas. US.
Nieuwdorp et al.. Increased plasma hyaluronan as novel predictor for atherosclerotic vulnerability in type 1 diabetes mellitus. Diabetologia, 2005, p. A410. vol. 48. No. Suppl. 1.
Nieuwdorp. et al., Perturbation of hyaluronan metabolism predisposes patients with type 1 diabetes mellitus to atherosclerosis. Diabetologia, Clinical and Experimental Diabetes and Metabolism, Apr. 6, 2007, pp. 1288-1293, vol. 50, No. 6.
Plaits, et al., Ischemia reperfusion induces a rapid modulation of the endothelial glycocalyx which is inhibited by activation of the adenosine A 2A receptor. FASEB Journal, Mar. 2003. p. Abstract 10119, vol. 17, No. 4-5. Federation of American Societies for Experimental Biology. Bethesda, US.
Henry et al., TNF-alpha increases entry of macromolecules into luminal endothelial cell glycocalyx, American Journal of Physiology: Heart and Circulatory Physiology. Dec. 2000, pp. H2815-H2823, vol. 279, No. 6. Pt. 2, The American Physiological Society.
Nieuwdorp et al., The endothelial glycocalyx: a potential barrier between health and vascular disease, Current Opinion in Lipidology, Oct. 2005, pp. 507-511, vol. 16. No. 5, London. GB.
PCT International Search Report, PCT/EP2008/066524, dated Mar. 23, 2009.
Japanese Office Action for co-pending application 2010-535403 dated Sep. 24, 2013.
Weinbaum et al., Mechanotransduction and flow across the endothelial glycocalyx, Proc Natl Acad Sci USA, Jun. 24, 2003, pp. 7988-7995, vol. 100, No. 13.

* cited by examiner

*Primary Examiner* — James Martinell
(74) *Attorney, Agent, or Firm* — TraskBritt, P.C.

(57) ABSTRACT

The invention relates to diagnostic and therapeutic tools and applications, particularly useful in diseases that affect vascular health and in inflammatory diseases. In particular, said diagnostic and therapeutic tools employ suitable detection or modulation of endothelial glycocalyx.

6 Claims, 25 Drawing Sheets

(C)

(D)

A

B c

A

C

A

A

B

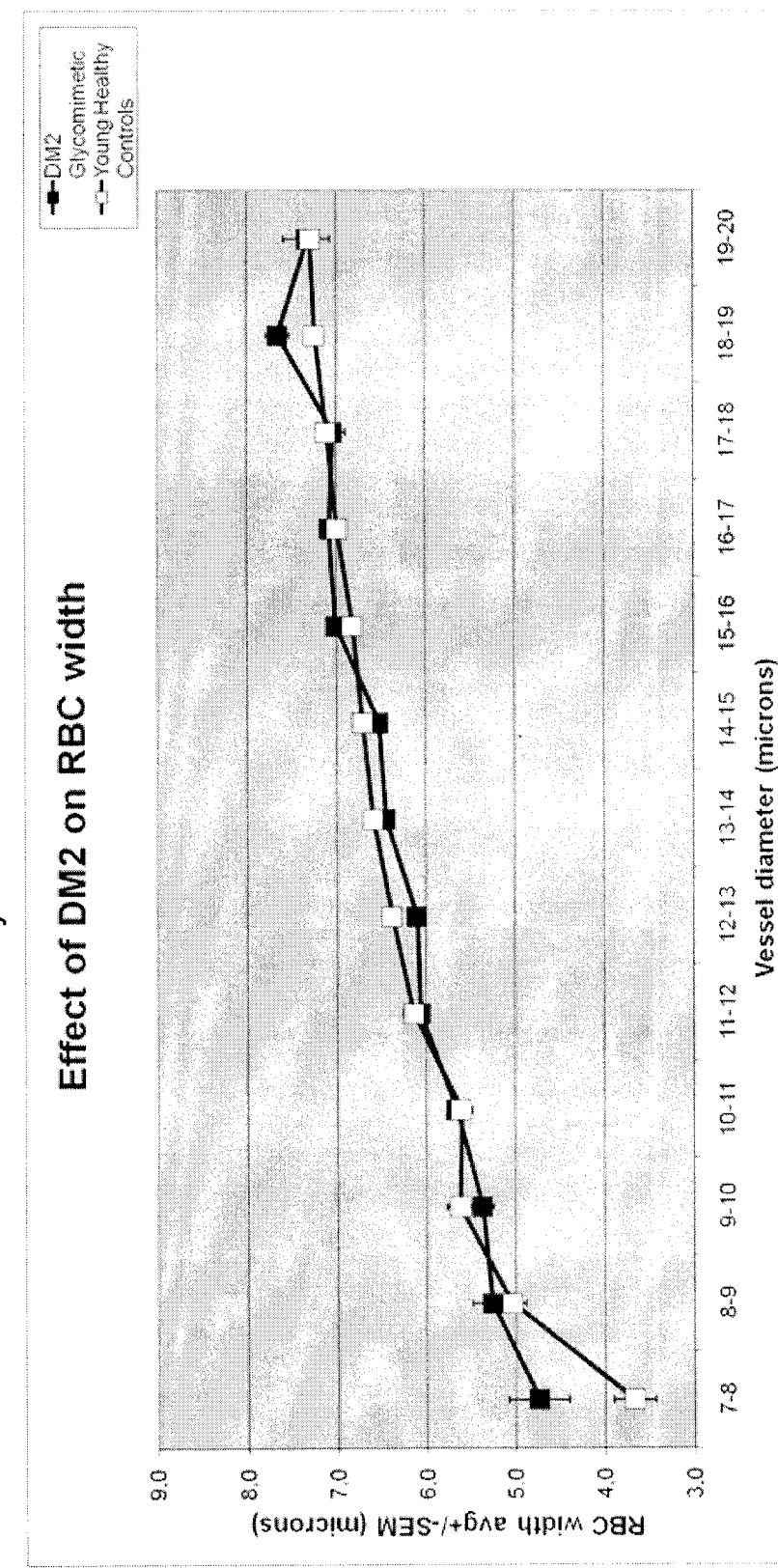

DIAGNOSTIC AND THERAPEUTIC TOOLS FOR DISEASES ALTERING VASCULAR FUNCTION

FIELD OF THE INVENTION

The invention relates to diagnostic and therapeutic tools and applications, particularly useful in diseases that affect vascular health and in inflammatory diseases. In particular, said diagnostic and therapeutic tools employ suitable detection or modulation of endothelial glycocalyx.

BACKGROUND OF THE INVENTION

Vascular diseases represent a principal cause of morbidity and mortality in modern human societies. While cardiovascular and cerebrovascular disorders, such as congestive heart failure and the catastrophic events of myocardial infarction, sudden cardiac death or stroke, are widely recognised, vascular dysfunction may as well obstruct blood supply to other organs or body parts, such as for example intestines, kidneys, upper or lower extremities (e.g., peripheral artery occlusive disease).

A central etiologic component of vascular diseases is atherogenesis, i.e., the progressive formation of atheromatous plaques in subintimal layer, which instigates inflammatory atherosclerotic lesions within arteries and arterioles. Plaque deposition may lead to arterial stenosis, causing inadequate blood supply to organs fed by the artery. More often, inflammation of the plaque may contribute to rupture of the fibrous cap resulting in thrombus formation and ensuing infarction.

Predisposition for, incidence and/or rate of progression of vascular pathogenic alterations, including inter alia endothelial dysfunction, increased vascular permeability, increased leukocyte and platelet aggregation and eventually atherogenesis and atherosclerosis, may be augmented in or associated with various risk factors or disease conditions, such as, among others, with acute and chronic inflammatory states and diseases, and with chronic vascular challenges. For instance, patients with chronic inflammatory disorders such as rheumatoid arthritis and systemic lupus erythematosus can suffer from accelerated atherogenesis (Solomon et al. 2003. Circulation 107: 1303-7; Roman et al. 2003. N Engl J Med 349: 2399-406); elevated levels of endotoxin in human bloodstream have been associated with an increased risk of atherosclerosis (Stoll et al. 2004. *Arterioscler Thromb Vasc Biol* 24: 2227-36); and repeated administration of endotoxin has been shown to increase atherosclerotic lesion formation in rabbits on a hypercholesterolemic diet (Lehr et al. 2001. Circulation 104: 914-20); and even single inflammatory challenges such as vaccination, infusion of C-reactive protein, or endotoxin administration may cause endothelial dysfunction in humans.

Consequently, there exists an urgent need for diagnostic tools capable of detecting the vulnerability of the vessel wall towards atherogenic stimuli, particularly in subjects and patient groups that may be at risk for developing vascular alterations or are suspected or known to suffer from vascular pathology. Moreover, there also exists a need for novel targets which allow for increasing the protective capacity of the vessel wall against atherogenic stimuli, thereby providing for further therapeutic and preventative measures.

SUMMARY OF THE INVENTION

The invention addresses the above discussed needs in the art.

More specifically, the invention teaches further diagnostic tools to detect vascular vulnerability and pathogenesis. Said diagnostic tools may preferably entail one or more advantages over previously known diagnostic approaches to vascular pathology, such as, for example, greater speed, sensitivity, specificity and/or simplicity of detection, earlier detection of vascular pathological changes, simultaneous detection of multiple relevant parameters, detection from less starting material or from starting material obtained by less or non-invasive techniques.

The invention teaches as well further manners to ameliorate vascular vulnerability and pathogenesis. The preventative or therapeutic interventions of the invention may preferably entail one or more advantages over previously known treatments for vascular pathology, such as inter alia greater efficacy, specificity and/or tolerability of the treatment, impact throughout various stages of disease including pre-onset or early stages of vascular dysfunction, action via novel mechanisms, possibly complementing existing therapies.

In particular, the present inventors have conclusively demonstrated that challenges which promote the development of vascular vulnerability and disease—such as for example inflammatory challenges—bring about demonstrable alterations in endothelial glycocalyx, such as, for instance, reduced systemic and microvascular glycocalyx volume or dimension, increased glycocalyx permeability, shedding of glycocalyx components such as hyaluronan and heparan sulphate, and altered levels of enzymes that participate in glycocalyx metabolism.

Also in view of the significance of endothelial integrity (including glycocalyx functions) for vascular health, the inventors thus contemplate that monitoring of glycocalyx-related parameters or markers can provide valuable information on the risk or presence of vascular dysfunction and disease, as well as the atherogenic susceptibility to inflammatory challenges. In addition, the inventors also contemplate that prophylactic and/or therapeutic interventions aimed at protecting and/or reconstituting glycocalyx integrity (for example, by replenishing glycocalyx constituents, stimulating glycocalyx build up or by inhibiting glycocalyx breakdown), can prevent or improve the prognosis of vascular dysfunction and diseases, as well as of inflammation, and of atherogenic susceptibility to inflammatory challenges.

Accordingly, in an aspect the invention provides a method for diagnosing vascular disease or the susceptibility to vascular disease in a subject, comprising detecting in said subject an alteration in the status, volume or dimension of glycocalyx, permeability of glycocalyx, shedding of glycocalyx and/or the activity of one or more enzymes of glycocalyx metabolism. By means of example and not limitation, alterations in these aspects of glycocalyx homeostasis can be compared to control subject or subjects not having vascular disease or susceptibility to vascular disease, to assess whether a significant difference occurs that may be indicative of the pathological phenotype.

In a further aspect, the invention provides a method for diagnosing atherogenic susceptibility to inflammatory challenges in a subject, comprising detecting in said subject an alteration in the status, volume or dimension of glycocalyx, permeability of glycocalyx, shedding of glycocalyx and/or the activity of one or more enzymes of glycocalyx metabolism. By means of example and not limitation, alterations in these aspects of glycocalyx homeostasis can be compared to control subject or subjects not exposed to inflammatory challenges, to assess whether a significant difference occurs that may be indicative of the pathological phenotype.

In embodiments, said perturbation in the status, volume or dimension of glycocalyx, permeability of glycocalyx, shedding of glycocalyx and/or the activity of one or more enzymes of glycocalyx metabolism, may be detected, without limitation, in individual blood vessels (such as, e.g., in individual arteries or arterioles), at the level of tissues, body parts, organs and/or at the systemic level.

Preferably in the above-defined diagnostic methods, measurements necessary to determine the status, volume or dimension of glycocalyx, permeability of glycocalyx, shedding of glycocalyx and/or the activity of one or more enzymes of glycocalyx metabolism, may be performed on a biological sample removed from a subject. Such in vitro assays are generally easy to perform and amenable to high-throughput analysis. Suitable samples include, without limitation, samples of whole blood, plasma or serum obtained from a subject. These body fluids are in vivo in direct contact with the vascular endothelial tissue and therefore are responsive to glycocalyx perturbation. Moreover, at least some glycocalyx indicators, such as for example but without limitation glycocalyx associated lectin-like proteins, may also be detectable in urine samples.

In an embodiment, glycocalyx perturbation may be diagnosed in samples removed from subjects, such as e.g. blood, plasma or serum samples, comprising detecting in said samples the presence and/or concentrations of inter alia glycocalyx-derived molecules such as, e.g., oligo- or poly-saccharides, glycosaminoglycans, hyaluronan, heparan sulphate or proteoglycans; enzymes that catalyse glycocalyx anabolism or catabolism, such as, e.g., hyaluronidase; and/or endogenous or exogenous (e.g., infused) substances that can become incorporated or otherwise associate with glycocalyx, and can thus provide information about (systemic) glycocalyx volume or dimension and/or its molecular accessibility. By means of example but without limitation, profiles of endogenous lectin-like proteins that normally associate with glycocalyx, as determined in samples e.g. in plasma or urine samples, can provide suitable information about glycocalyx volume or dimension and/or its molecular accessibility. By means of example and not limitation, alterations in indicators or markers of glycocalyx homeostasis such as stated above can be compared to control subject or subjects to assess whether a significant difference occurs that may be indicative of a pathological phenotype.

In an embodiment, the presence and/or concentration of the above or other glycocalyx markers may be, sequentially or simultaneously, detected by assay technologies known in the art, such as immunoprecipitation, enzyme-linked immunosorbent assay (ELISA), radio-immunoassay (RIA), colorimetric and fluorimetric enzyme activity assays, etc.

In another preferred embodiment of the present invention, the status of the glycocalyx can be determined by a size distribution method in which the endothelial glycocalyx dimension of individual capillary blood vessels or the Glycocalyx width (GW) is determined. Additionally, the size distribution method can also provide measurements for the width of red blood cells (RBCW) in the blood vessels, the vessel diameter (VD) and the Capillary Volume Reserve (CVR). Hence, no samples are to be removed from the test subject. The use of the size distribution method and technology may bring about one or more advantages such as, for example, speed of throughput, reduced stress on patients and sample-collecting personnel; lower cost detection, automated comparison with references, portable apparatuses, faster detection; and/or avoidance of laborious and logistically demanding laboratory-based techniques and personnel; etc. A further advantage of the method and apparatus of the present invention is the individualized monitoring at home, enabling a (semi-)permanent watch of the status, for instance via a connection to a centralized and/or operated work station. Accordingly, the invention provides for diagnosing vascular disease or atherogenic susceptibility to inflammatory challenges in subjects.

Accordingly, the invention also provides a Glycocalyx monitor (GM) device configured to detect the glycocalyx status, and/or influence of compounds on glycocalyx status such as, for instance, enzymes catalysing glycocalyx anabolism or catabolism, and/or an endogenous or exogenous substance that can become incorporated or otherwise associate with glycocalyx, such as e.g. endogenous lectin-like proteins that normally associate with glycocalyx.

Also, the invention relates to a kit comprising the above-defined Glycocalyx monitor, software, and optionally one or more buffers, reagents, calibration analytes, positive and/or negative control, and/or instructions for use, required for performing a diagnostic method using said Glycocalyx monitor.

In another preferred embodiment, the presence and/or concentration of the above or other glycocalyx markers may be, sequentially or simultaneously, detected using a biosensor device. Biosensors favourably combine a sensitive and specific biological component (such as, e.g., a receptor with high affinity and specificity for binding with a to-be-detected analyte; or an enzyme that catalyses a reaction involving a to-be-detected analyte; or a substrate of a to-be-detected enzyme), with a physical, chemical or physicochemical detector component that allows to monitor the biological event (such as, e.g., said binding or reaction). The use of biosensor technology may bring about one or more advantages, such as, for example: the use of smaller sample volumes, which can step up throughput and diminish the stress on patients and sample-collecting personnel; possibility of simultaneous detection of two or more markers in one sample; disposable, portable and potentially low cost detection; faster detection; and/or avoidance of laborious and logistically demanding laboratory-based techniques; etc.

Accordingly, the invention also provides a biosensor device configured to detect, in a sample removed from a subject, the presence and/or concentrations of a glycocalyx-derived molecule, an enzyme that catalyses glycocalyx anabolism or catabolism, and/or an endogenous or exogenous substance that can become incorporated or otherwise associate with glycocalyx, such as e.g. endogenous lectin-like proteins that normally associate with glycocalyx.

Also, the invention relates to a kit comprising the above-defined biosensor device, and optionally one or more buffers, reagents, calibration analytes, positive and/or negative control, and/or instructions for use, required for performing a diagnostic method using said biosensor device.

The invention further concerns the use of the biosensor device as defined above or kit comprising such, in the above-defined diagnostic methods of the invention for diagnosing vascular disease or atherogenic susceptibility to inflammatory challenges in subjects.

In other embodiments, some diagnostic methods may need to be carried out on the body of a subject. By means of example and not limitation, the status and/or thickness of endothelial glycocalyx in individual capillary blood vessels can be measured in human and other subjects by orthogonal polarization spectral (OPS) imaging of the sublingual microcirculation, as shown in the examples. By means of another example, glycocalyx in individual vessels of subjects, primarily animal subjects, can be examined using invasive microscopic visualisation techniques which comprise injection of fluorescent labels attached to glycocalyx-bound proteins or glycocalyx permeating tracer molecules. By means of a further example, the glycocalyx status can be monitored or determined by the size distribution method of the present invention, which is a non-invasive method. Preferably, the size distribution method is performed with a Glycocalyx monitor.

A further aspect relates to the use of a glycocalyx constituent for the manufacture of a medicament for the treatment of a vascular disease, for reducing atherogenic susceptibility to inflammatory challenges, or for the treatment of an inflammatory disease. A related aspect concerns a glycocalyx constituent for use as a medicament, or for use in the treatment of vascular disease, for reducing atherogenic susceptibility to inflammatory challenges, or for the treatment of an inflammatory disease. Also provided is a pharmaceutical composition comprising a glycocalyx constituent, particularly for use in the treatment of vascular disease, for reducing atherogenic susceptibility to inflammatory challenges, or for use in the treatment of an inflammatory disease. As well disclosed is a method for treating vascular disease, for reducing atherogenic susceptibility to inflammatory challenges, or for the treatment of an inflammatory disease, in a subject in need of such treatment, comprising administering to said subject a therapeutically or prophylactically effective amount of a glycocalyx constituent.

Another aspect relates to the use of an inhibitor of an enzyme of glycocalyx catabolism for the manufacture of a medicament for the treatment of vascular disease, for reducing atherogenic susceptibility to inflammatory challenges, or for the treatment of an inflammatory disease. A related aspect concerns an inhibitor of an enzyme of glycocalyx catabolism for use as a medicament, or for use in the treatment of vascular disease, for reducing atherogenic susceptibility to inflammatory challenges, or for use in the treatment of an inflammatory disease. Also provided is a pharmaceutical composition, comprising an inhibitor of an enzyme of glycocalyx catabolism, particularly for use in the treatment of vascular disease, for reducing atherogenic susceptibility to inflammatory challenges, or for use in the treatment of an inflammatory disease. As well disclosed is a method for treating vascular disease, for reducing atherogenic susceptibility to inflammatory challenges, or for the treatment of an inflammatory disease, in a subject in need of such treatment, comprising administering to said subject a therapeutically or prophylactically effective amount of an inhibitor of an enzyme of glycocalyx catabolism.

It shall be appreciated that the above diagnostic methods and therapeutic interventions may be used in combination or synchrony, particularly to advantageously tailor treatment to individual patients. For instance, where a diagnostic assay as above determines that one or more particular constituents of glycocalyx are significantly diminished in a patient, the treatment in said patient may be subsequently aimed at replenishing said constituent(s). In another example, where a diagnostic assay as above determines that one or more particular glycocalyx-degrading enzymes are overactive in a patient, the treatment in said patient may then aim to inhibit said enzyme(s). Accordingly in embodiments, a suitable prophylactic or therapeutic intervention as defined herein may be determined or decided on the basis on the diagnostic assays of the invention.

Also, the present diagnostic methods and devices (e.g., biosensors, size distribution method and/or the Glycocalyx monitor) can be used to monitor, even in individual patients, the effectiveness of any therapeutic interventions in vascular diseases or inflammation (e.g., of treatments as disclosed herein; or other treatments, such as inter alia medication to improve insulin sensitivity in diabetic patients, heparin therapy in cancer patients, existing treatments designed to improve endothelial function in inflammatory diseases, etc.), with respect to glycocalyx status and parameters such as volume or dimension, permeability, shedding, activity of glycocalyx metabolic enzymes, etc.

As noted, inflammation tends to increase the chances of developing vascular pathology. Hence, in an embodiment, the above-defined diagnostic methods to determine the presence of or risk for vascular disease, or for determining atherogenic susceptibility to inflammatory challenges, and/or the above-defined treatments of vascular diseases involving glycocalyx modulation, can be particularly useful in subjects with inflammation, for example, in patients having an inflammatory condition or disease.

As also noted, vascular pathology may be associated with a variety of risk factors and challenges, such as chronic vascular challenges. Thus, in an embodiment, the above-defined diagnostic methods to determine the presence of or risk for vascular disease, and/or the above-defined treatments of vascular diseases involving glycocalyx modulation, can be particularly useful in subjects having one or more risk factors chosen from age, smoking, hyperglycaemia and dyslipidemia; and/or in subjects having one or more risk pathologies chosen from ischemia-reperfusion injury, type 1 diabetes, type 2 diabetes, hyperglycaemia, insulin resistance, metabolic syndrome, dyslipidemia, hypercholesterolemia, hypertriglyceridemia, hypertension, cancer, infectious disease and trauma.

These and further aspects and preferred embodiments of the invention are described in the following sections and in the appended claims.

LPS+saline, diamonds: LPS+Etanercept). Data are presented as mean±SEM (*p<0.05 vs. baseline, i p<0.01 vs. baseline, # p<0.05 between groups).

Figure 4:
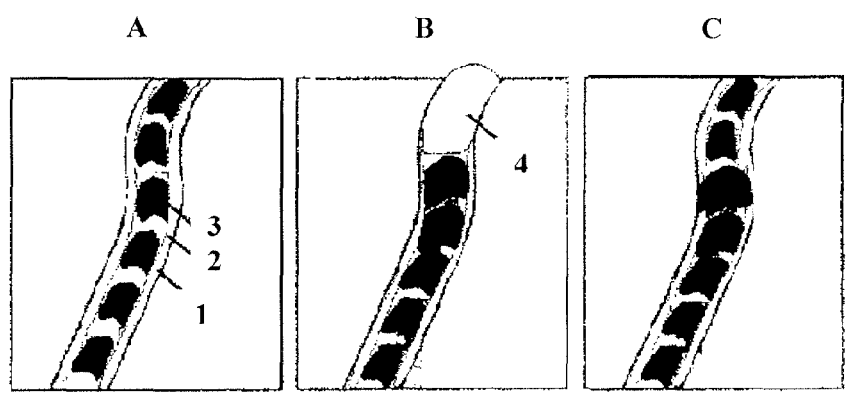

FIG. 4. Representation of the measurement method of the present invention, compared to prior art measurement methods.

Figure 5:
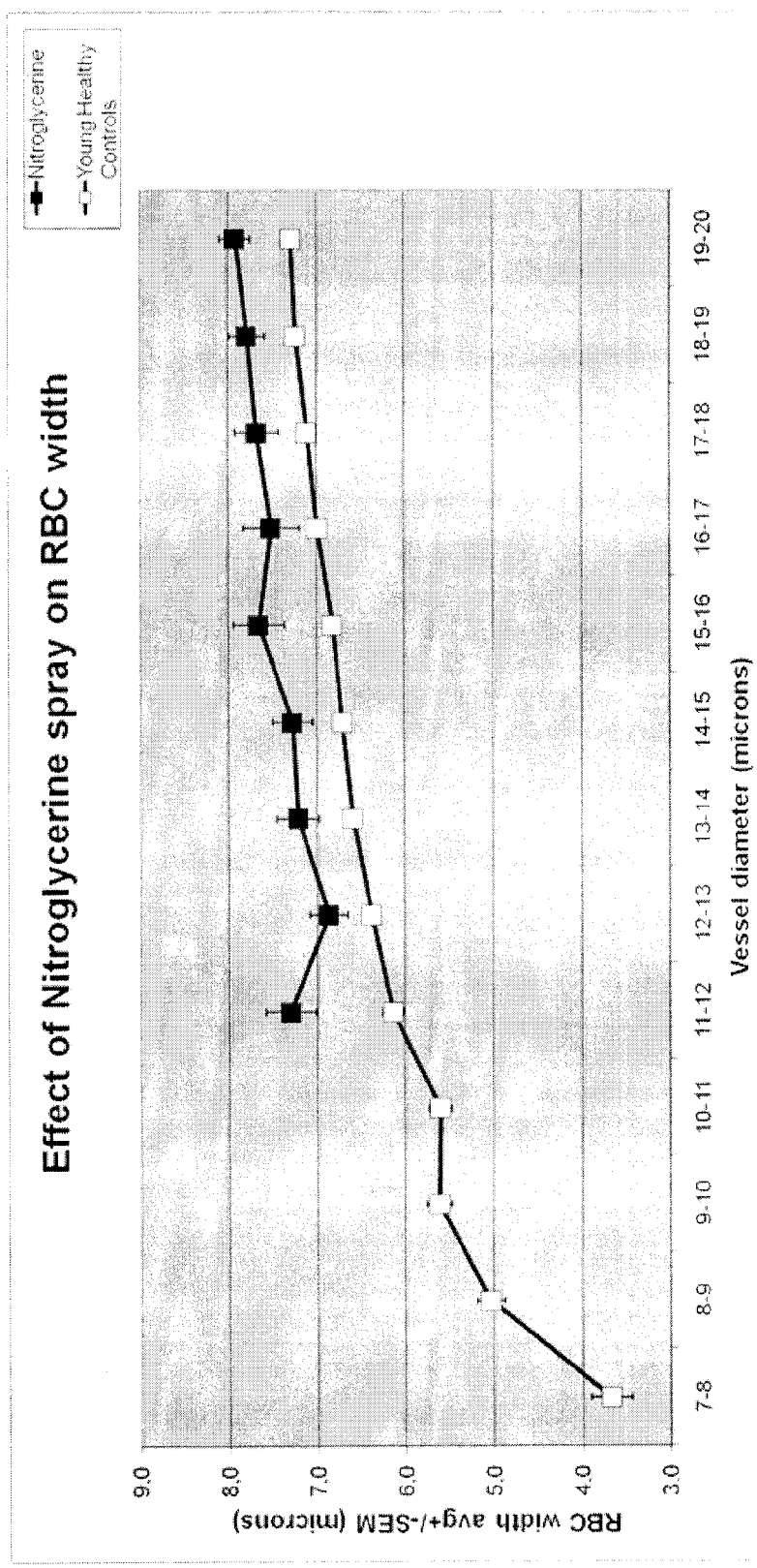
Figure 5:
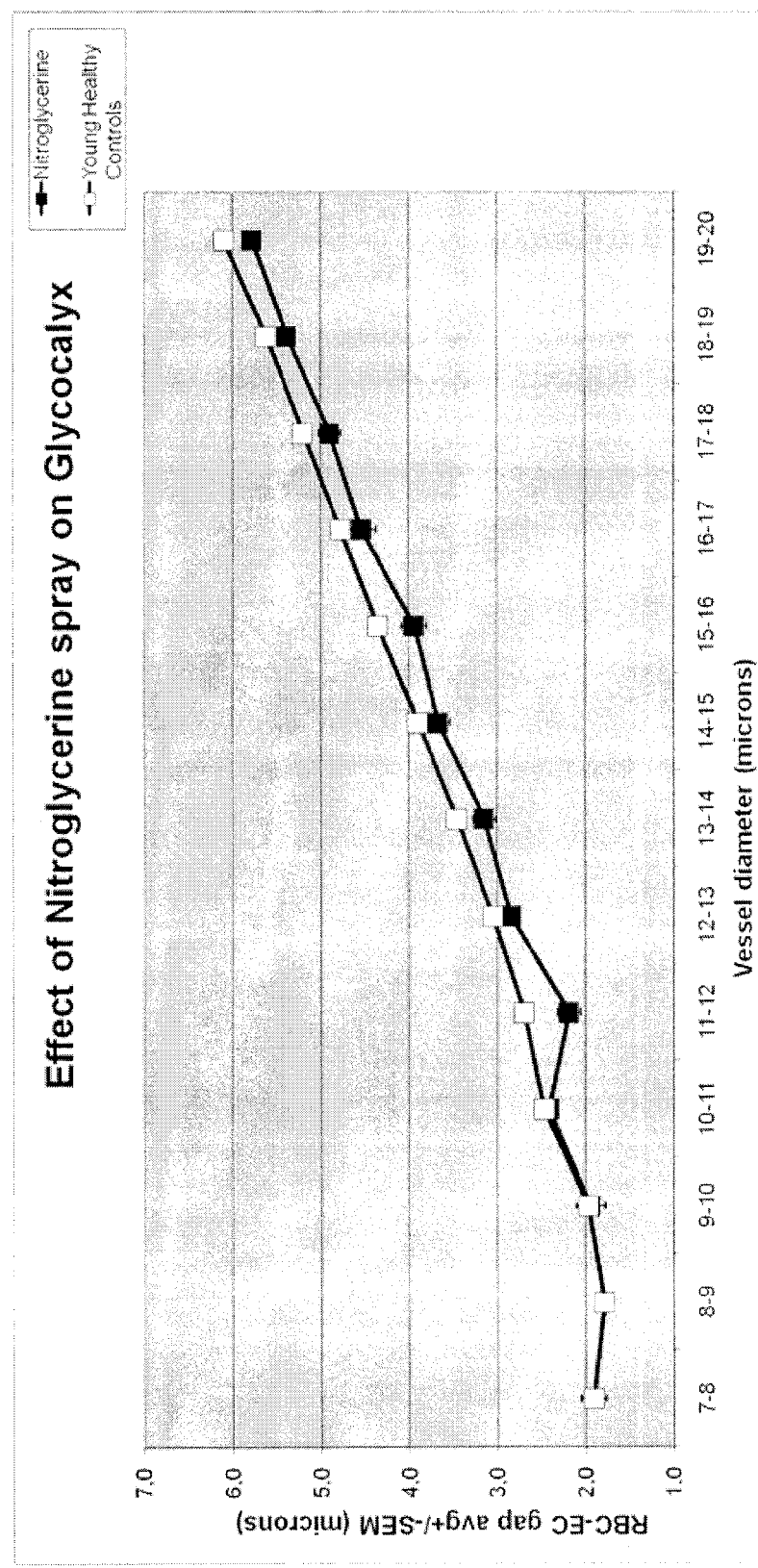
Figure 5:
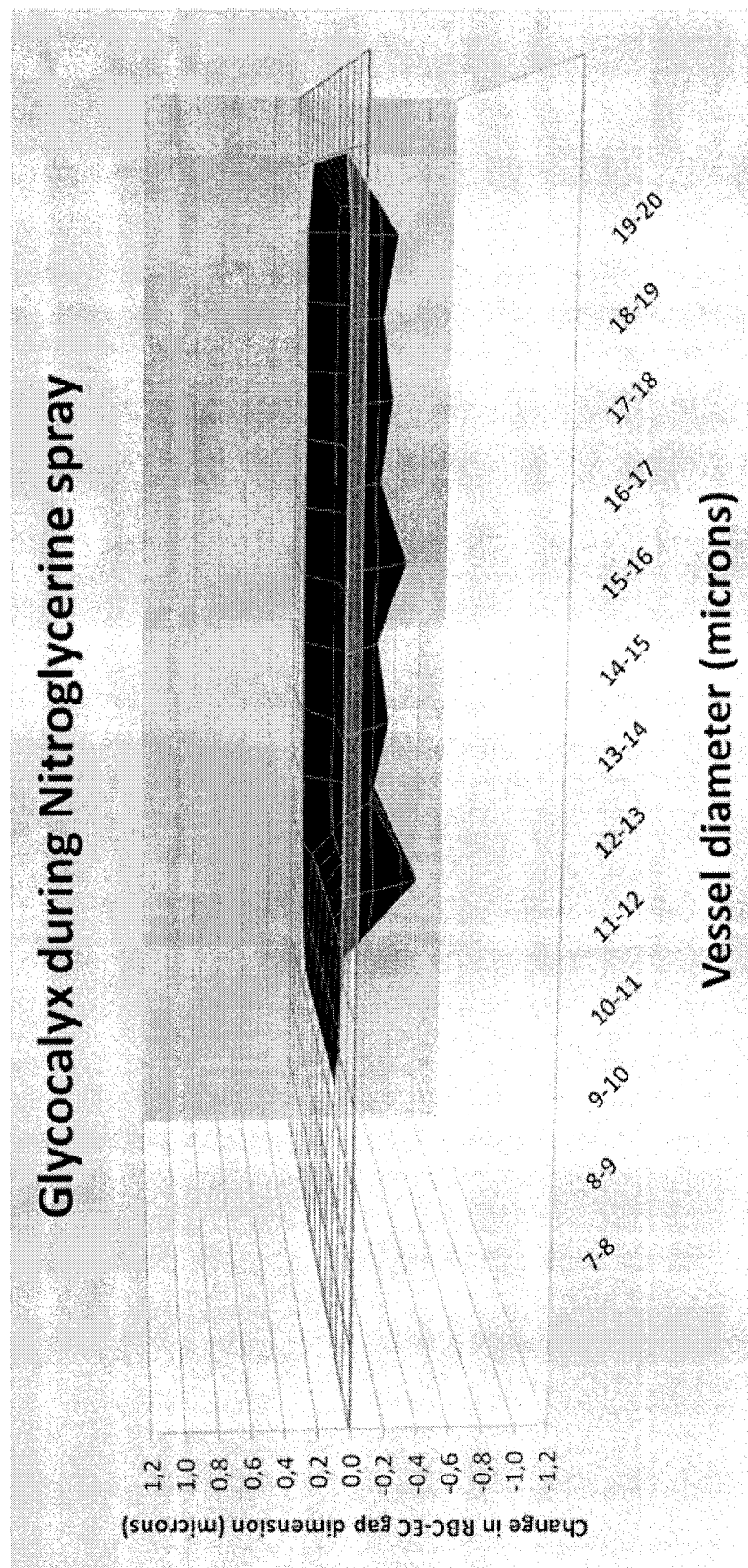

FIG. 5. Representation of the vessel diameter in function of the measured Red Blood Cell width (FIG. 5A), the glycocalyx width (FIG. 5B) and change in glycocalyx width relative to healthy controls (FIG. 5C) in the presence and the absence of nitroglycerine.

Figure 6:
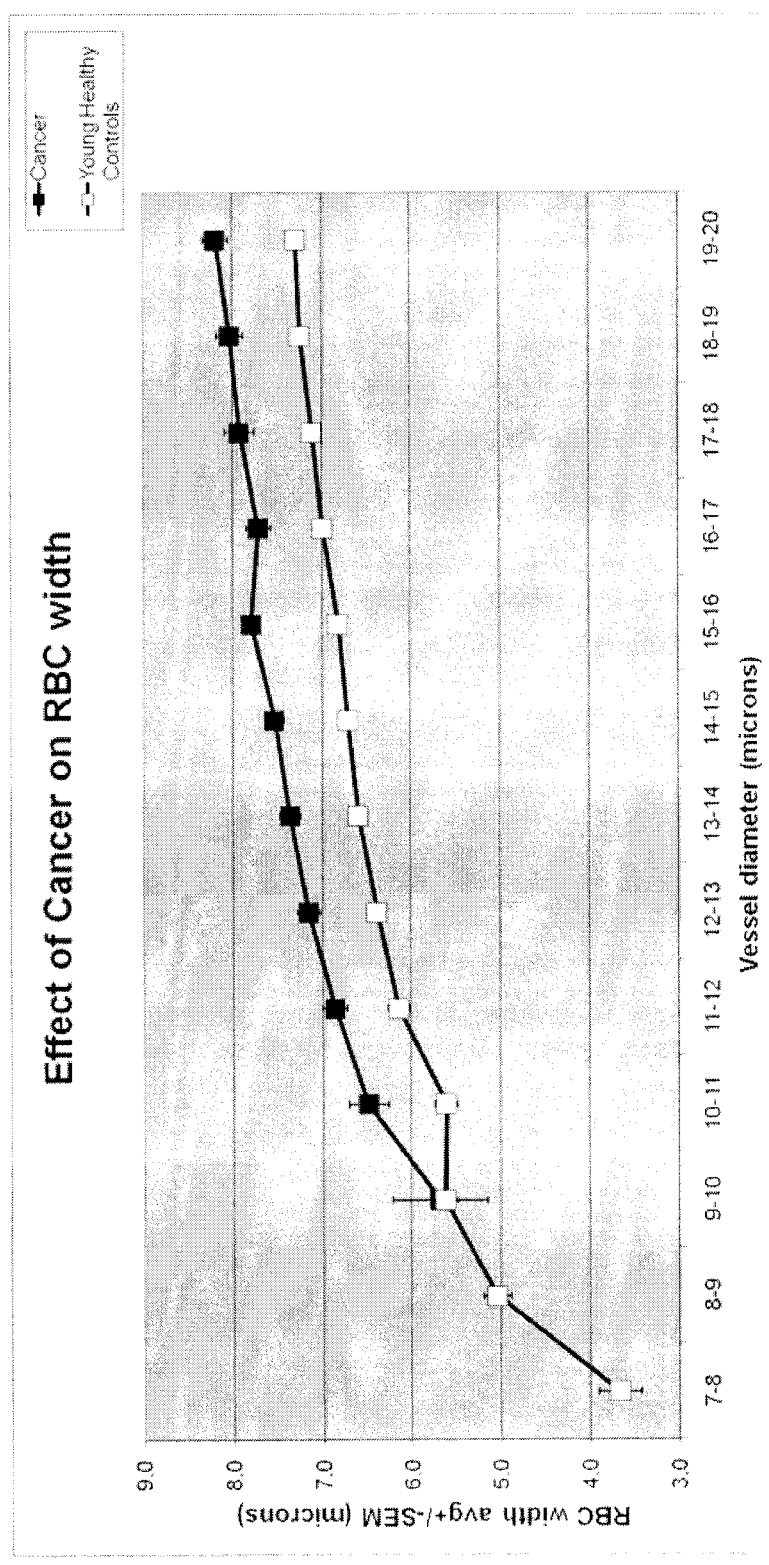
Figure 6:
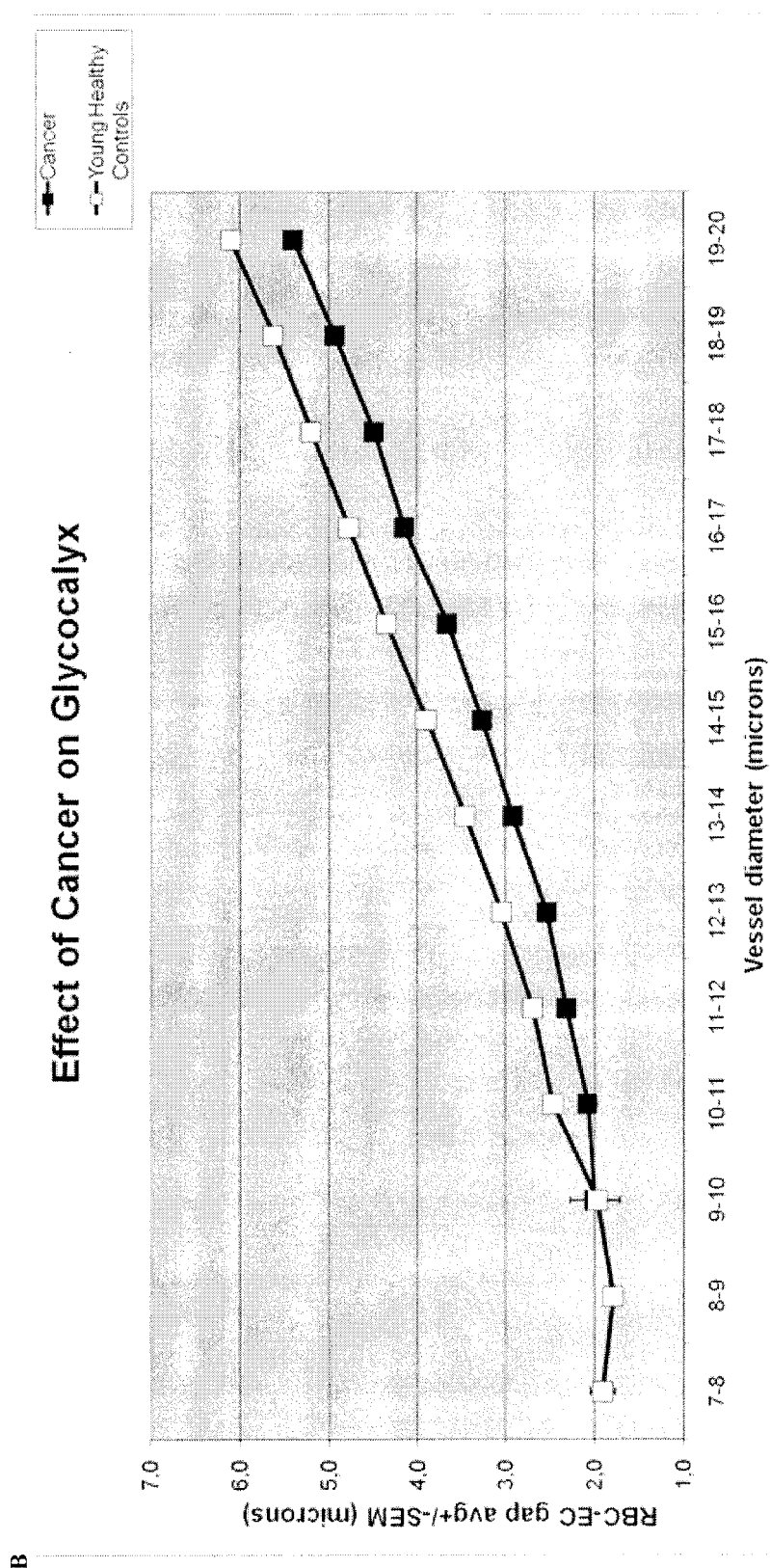
Figure 6:
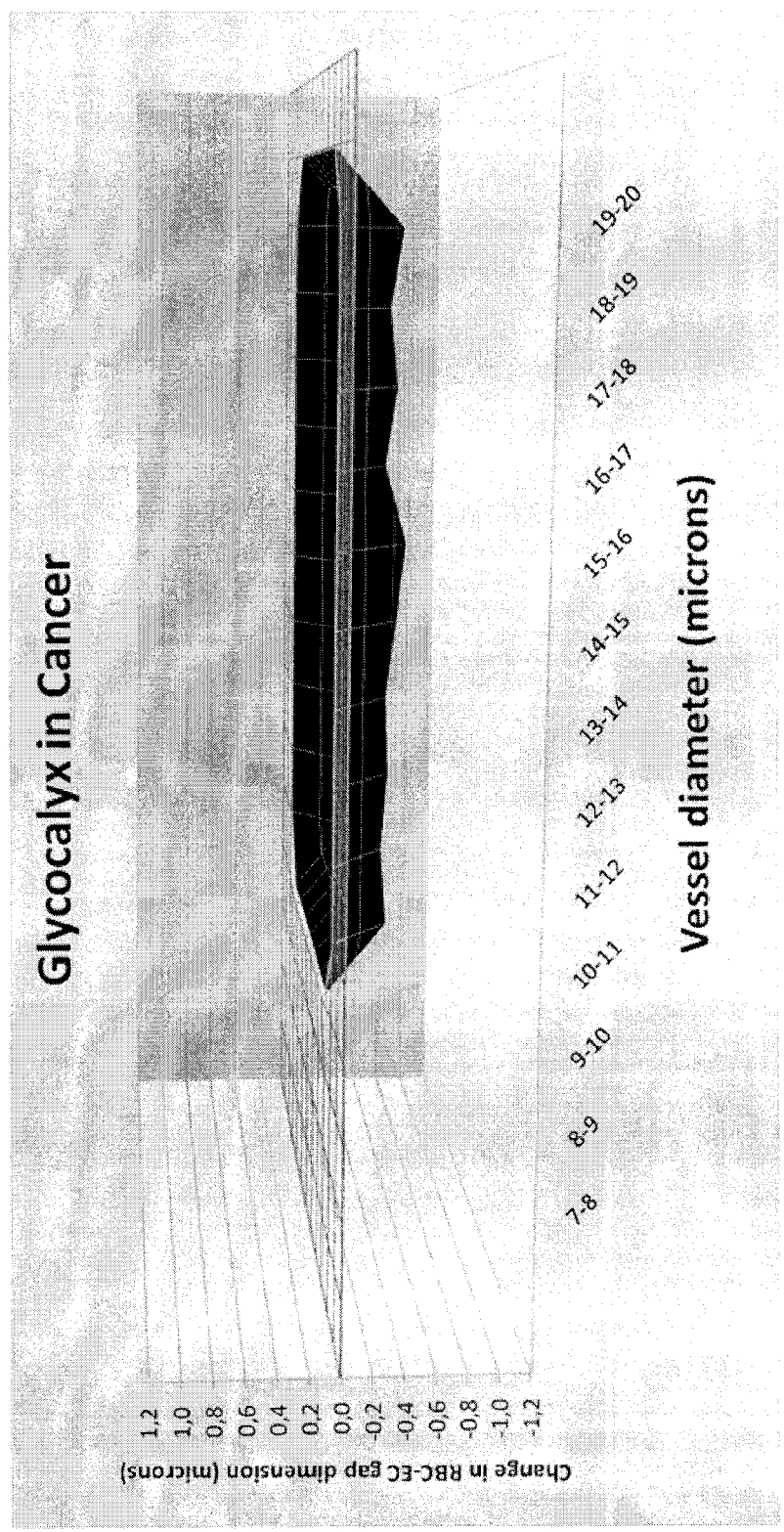

FIG. 6. Representation of the vessel diameter in function of the measured Red Blood Cell width (FIG. 6A) and the glycocalyx width (FIG. 6B) in healthy control subjects and cancer subjects and change in glycocalyx width relative to healthy controls (FIG. 6C).

Figure 7:
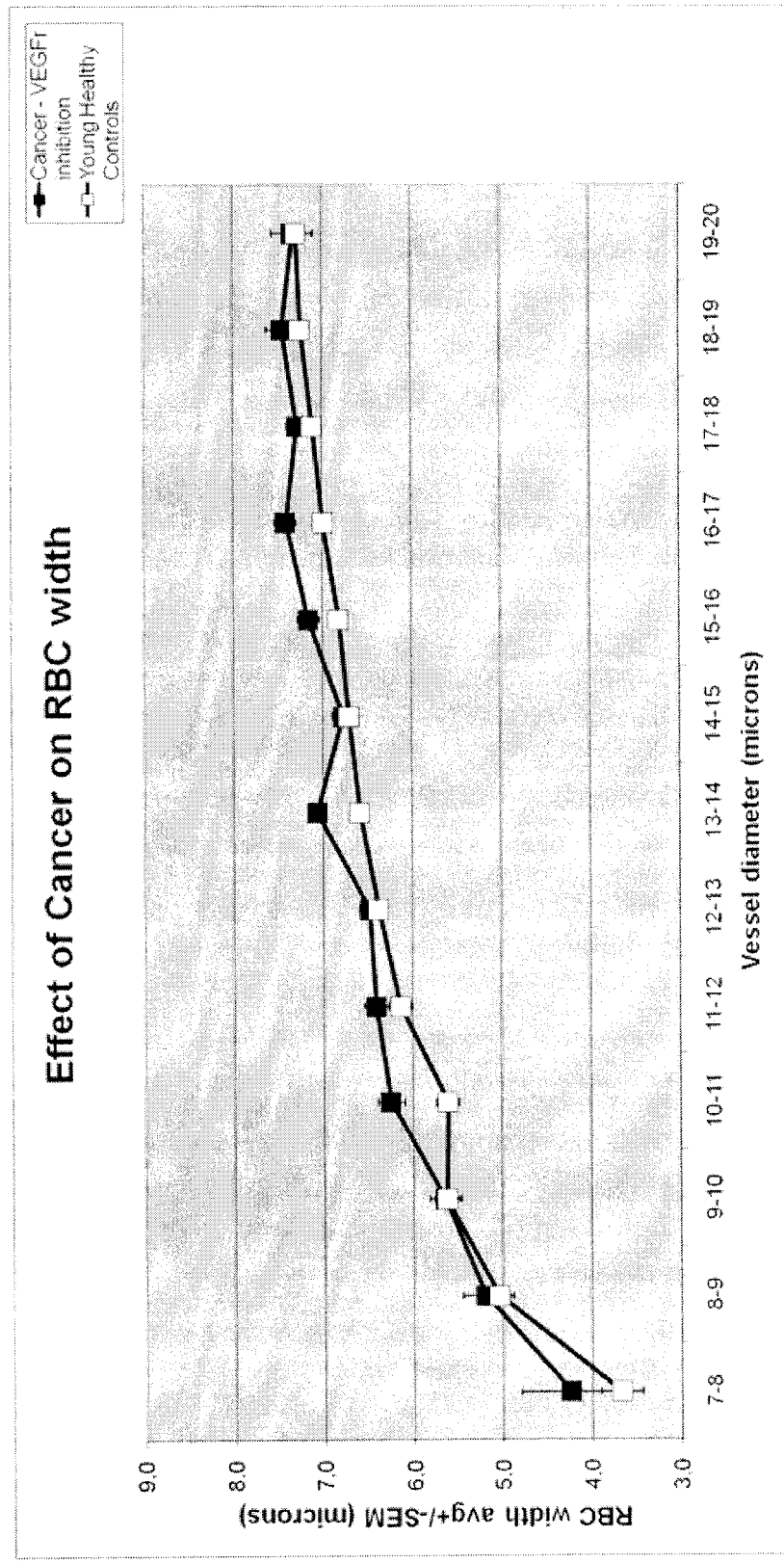
Figure 7:
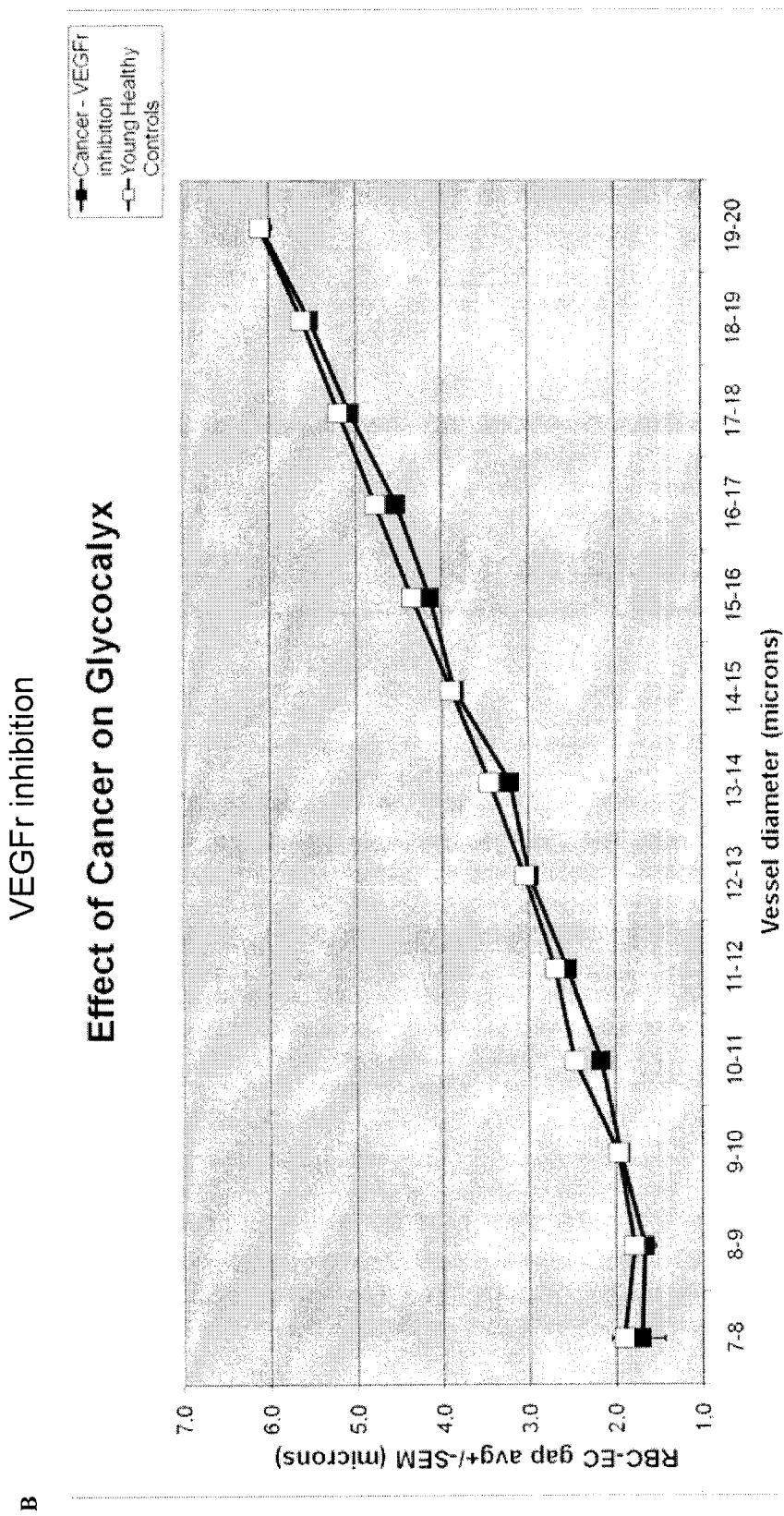
Figure 7:
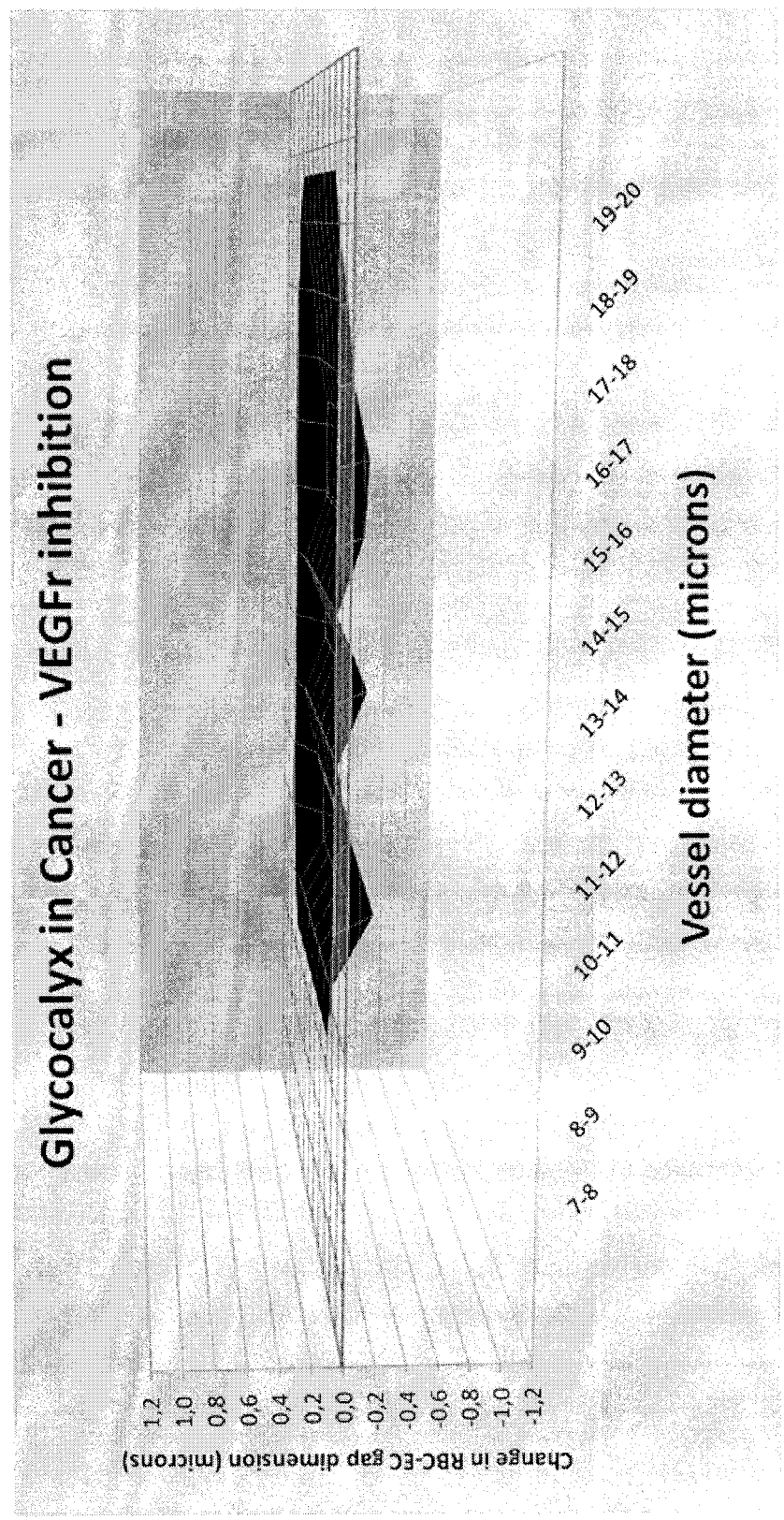

FIG. 7. Representation of the vessel diameter in function of the measured Red Blood Cell width (FIG. 7A) and the glycocalyx width (FIG. 7B) in healthy control subjects and cancer subjects upon treatment with VEGF receptor inhibiting compound and change in glycocalyx width relative to healthy controls (FIG. 7C).

Figure 8:
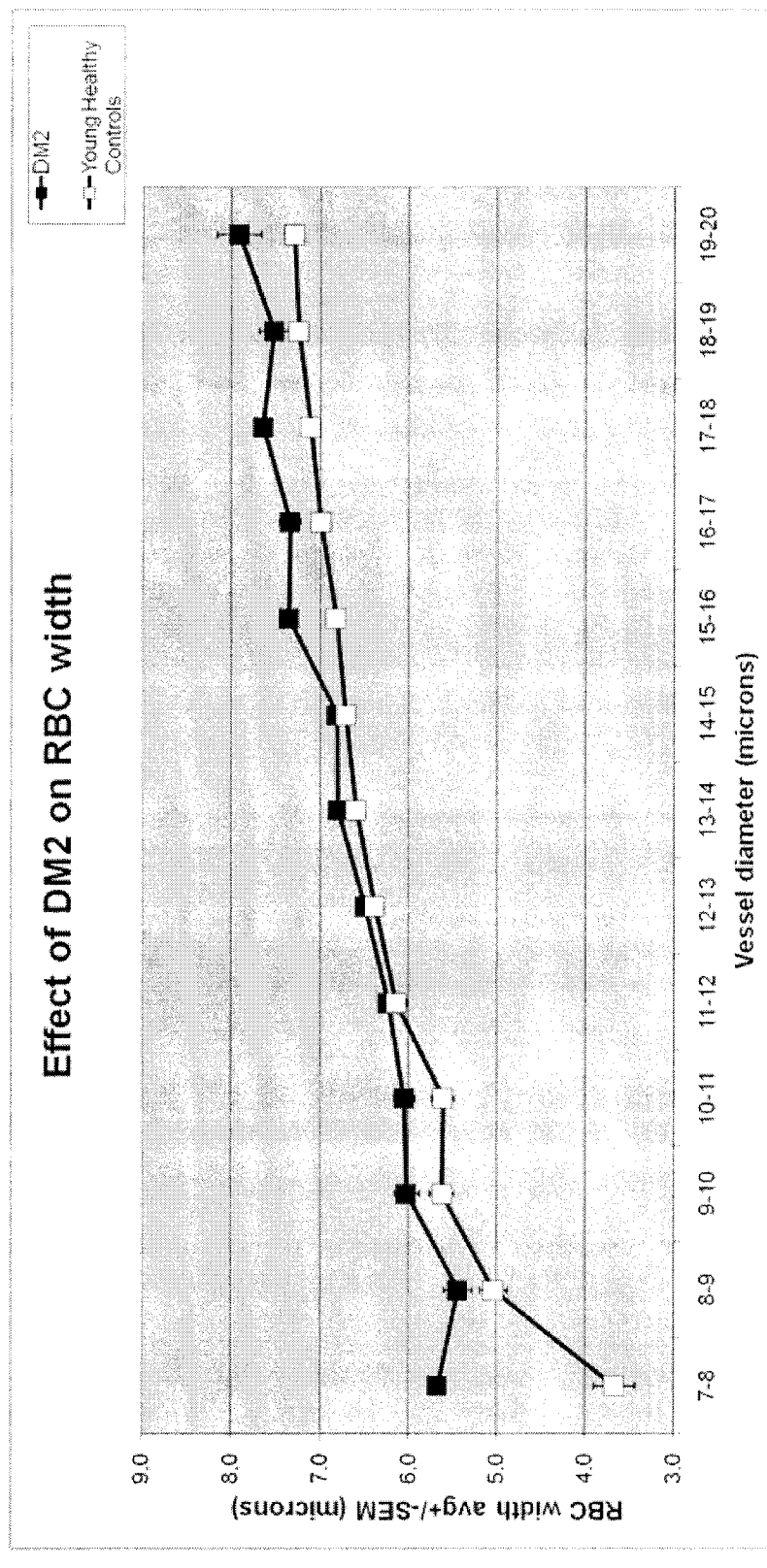
Figure 8:
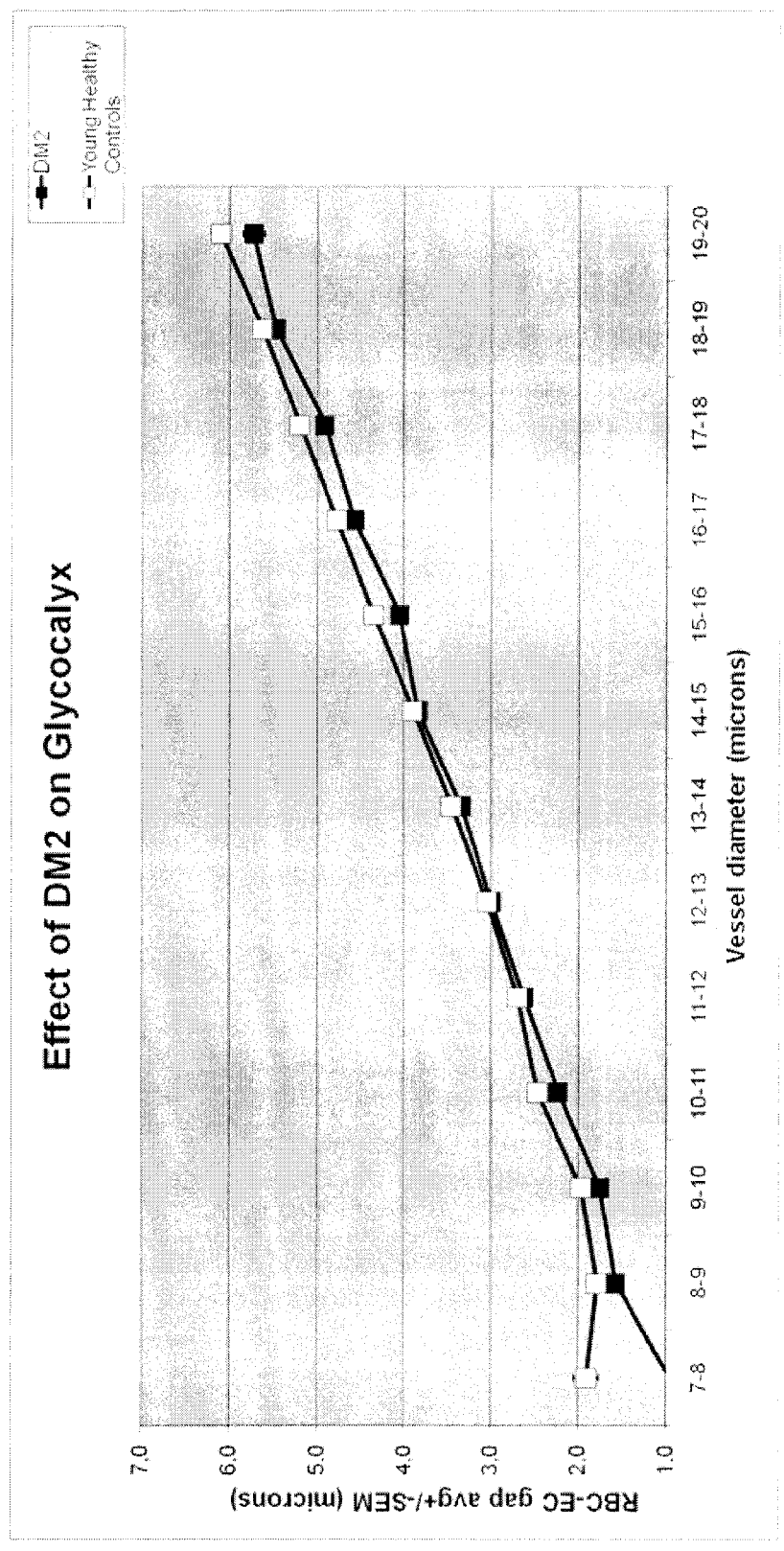
Figure 8:
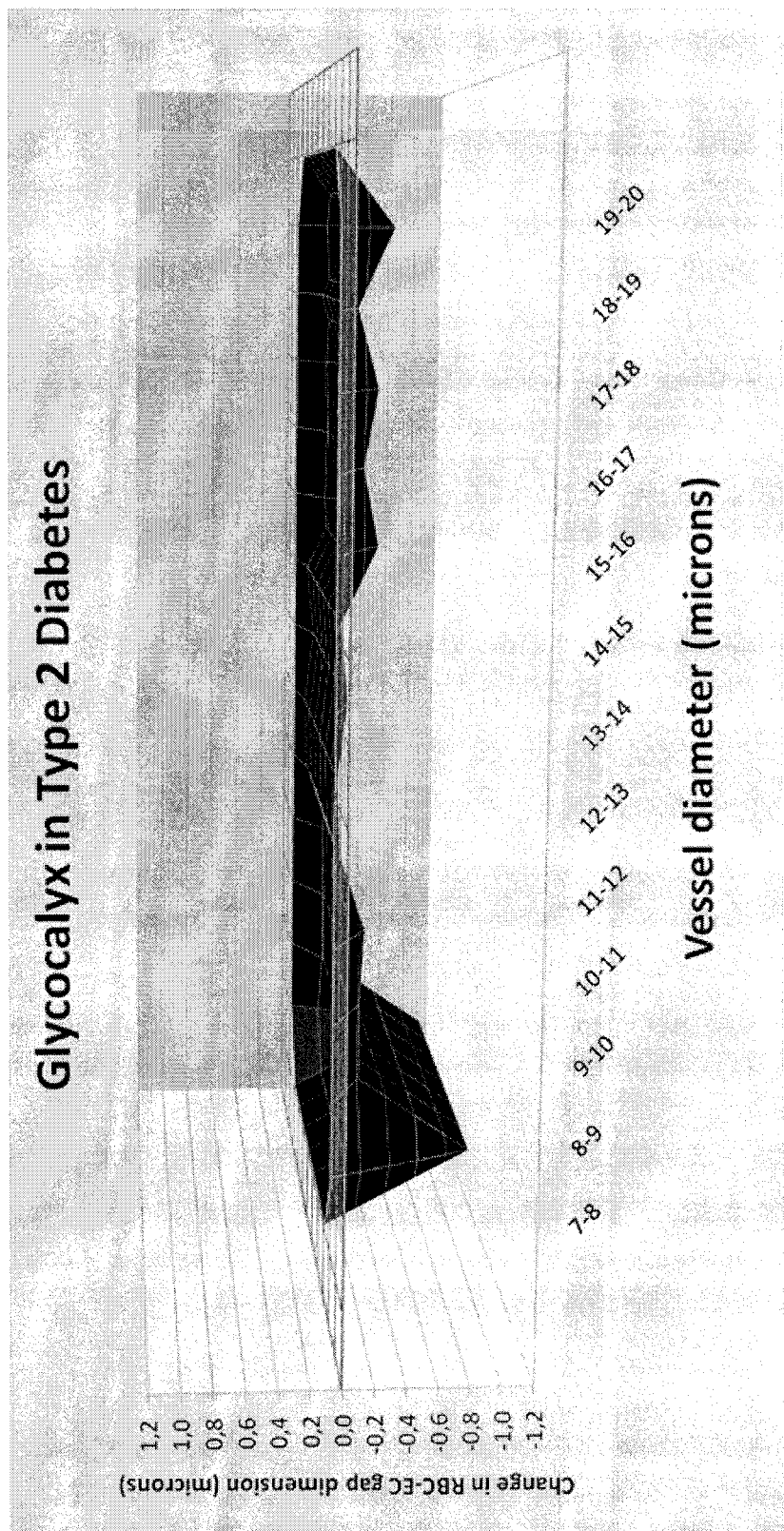

FIG. 8. Representation of the vessel diameter in function of the measured Red Blood Cell width (FIG. 8A) and the glycocalyx width (FIG. 8B) in healthy control subjects and diabetic subjects and change in glycocalyx width relative to healthy controls (FIG. 8C).

Figure 9:
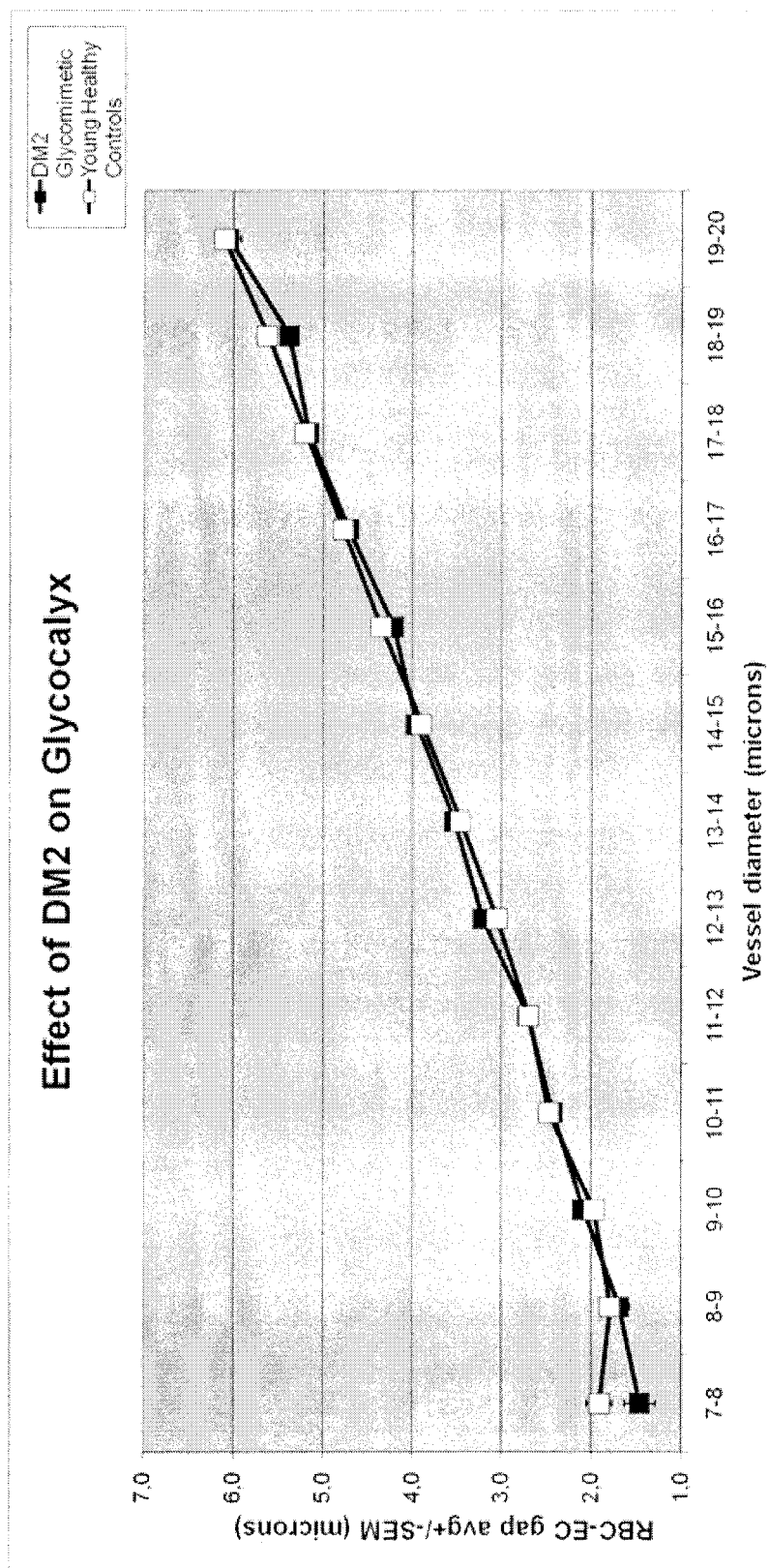
Figure 9:
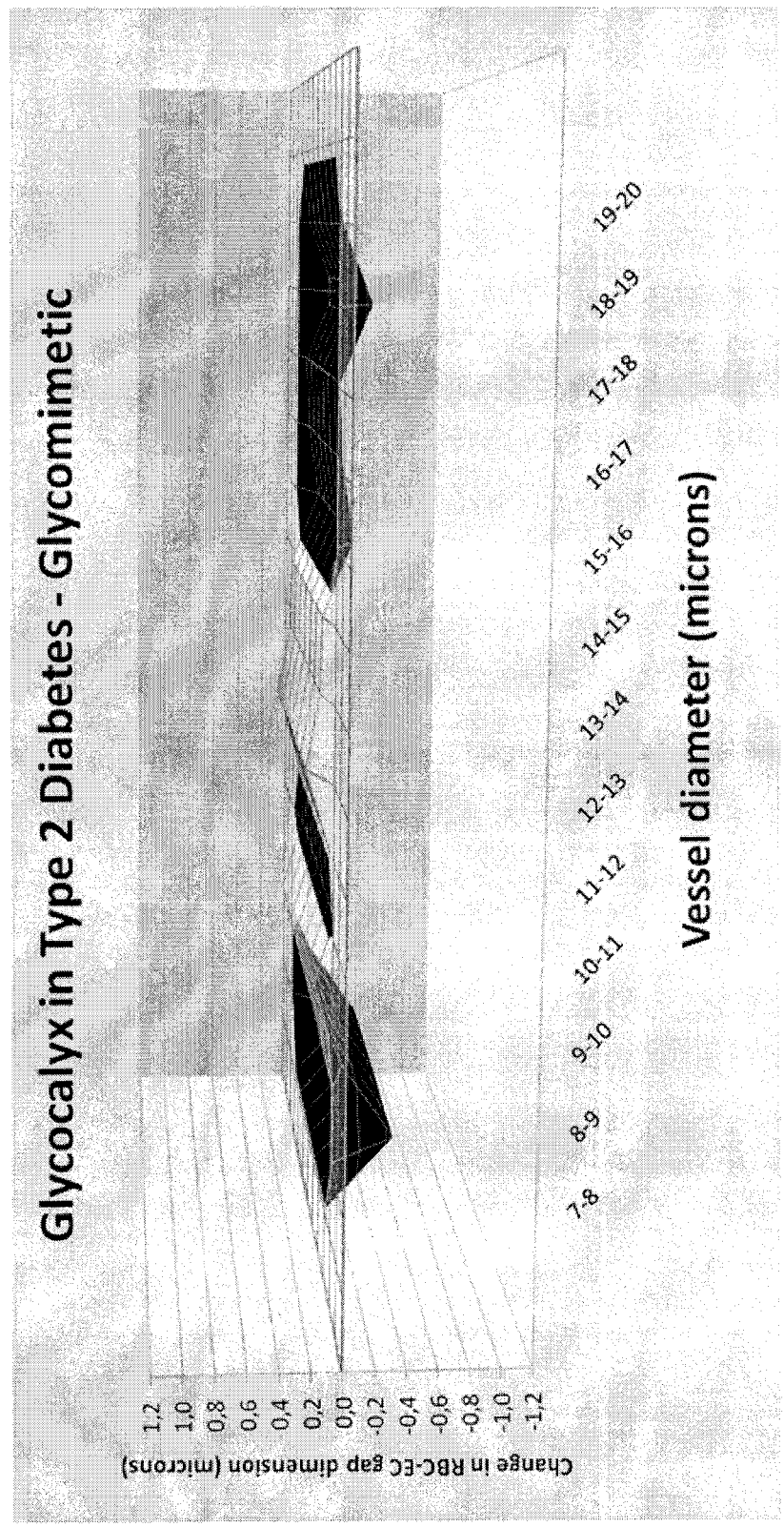

FIG. 9. Representation of the vessel diameter in function of the measured Red Blood Cell width (FIG. 9A) and the glycocalyx width (FIG. 9B) in healthy control subjects and diabetic subjects upon treatment with a glycomimetic compound and change in glycocalyx width relative to healthy controls (FIG. 9C).

DETAILED DESCRIPTION OF THE INVENTION

Definitions

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The terms "subject" or "patient" refer preferably to animals, more preferably warm-blooded animals, yet more preferably vertebrates, and even more preferably mammals specifically including humans and non-human mammals, that have been the object of treatment, observation or experiment. The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof.

As used herein, a phrase such as "a subject in need of treatment" includes subjects that would benefit from treatment of a given condition, such as vascular disease or inflammation. Such subjects may include, without limitation, those that have been diagnosed with said condition, those prone to develop said condition and/or those in whom said condition is to be prevented.

The term "sample" generally refers to material, in non-purified or purified form, obtained from a biological source. A biological sample may be typically removed from its biological source, such as from a subject of interest, by appropriate methods for collecting, drawing, biopsy or resection, etc. of bodily fluids, tissues, cells or the like. Particularly useful samples in the present invention include whole blood, plasma, serum and urine derived from subjects. A biological sample may be further processed to prepare suitable derivatives thereof, such as, without limitation, cell or tissue lysates, homogenates, supernatants, fractions, etc. A sample may be subdivided to isolate or enrich for parts thereof (such as, for example, parts that are expected to contain analytes of interest) to be used in the diagnostic methods of the invention. Hence, a sample can be applied to the methods of the invention directly or can be processed, extracted or purified to varying degrees before being used.

Disease Conditions

As noted in the Summary section, the invention describes diagnostic, prophylactic and therapeutic tools and methods particularly useful in vascular diseases and inflammation. In particular, the vascular diseases and inflammation can be further characterized by the status of the glycocalyx.

The term "vascular disease" as used herein refers to any disease, disorder or condition that affects the vascular system, including the heart and blood vessels. Vascular diseases include, without limitation, cardiovascular diseases, cerebrovascular diseases, peripheral vascular diseases, atherosclerosis and arteriosclerotic vascular diseases. The term encompasses presymptomatic vascular lesions, as well as vascular dysfunctions causing overt symptoms. For example, the term includes presymptomatic and symptomatic vascular dysfunction caused by stenosis, occlusion or aneurysm of blood vessels due to the development of atheromas and atherosclerotic plaques, and diseases and disorders resulting there from. Particular examples of vascular diseases include, without limitation, atherosclerosis, congestive heart failure, coronary artery disease (CAD), sudden cardiac death, myocardial infarction, ischemia, stroke, peripheral vascular diseases such as peripheral artery occlusive disease (PAOD), venous thromboembolism and pulmonary embolism.

The term "susceptibility" with reference to a disease denotes the susceptibility, likelihood, vulnerability or predisposition of a subject to a disease, such as, for example, to a vascular disease.

The term "inflammation" has the denotation given to it in the art. By means of further guidance, the term generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogenic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

The term "inflammation" as used herein particularly encompasses pathologies comprising an inflammatory component, including inter alia local and systemic, as well as acute and chronic inflammatory states, conditions or diseases. By preference but without limitation, the term may refer to any of the following conditions:

cachexia, e.g., cachexia associated with cancer or infectious diseases, such as, e.g., AIDS;

Gram-negative sepsis, endotoxin-induced shock, septic shock syndrome, systemic inflammatory response syndrome (SIRS) or multiple organ dysfunction syndrome (MODS);

vaccination;

graft versus host pathologies, such as, e.g., graft versus host disease (GVHD) or rejection of transplanted xenogenic or allogeneic tissues or organs, such as, e.g., rejection of allogeneic bone marrow or cord blood transplants;

acute and chronic infectious and parasitic processes, such as viral, bacterial or fungal, infections and protozoan or metazoan parasites, including, preferably, cerebral malaria or meningococcal meningitis;

allergic disorders, such as, e.g., allergic rhinitis, allergic conjunctivitis, asthma, eczema, urticaria, contact dermatitis, systemic allergic response (anaphylaxis) or anaphylactic shock, more preferably chosen from allergic rhinitis and asthma;

chronic inflammatory disorders (generally encompassing a heterogeneous group of conditions typically involving chronic or recurrent local or systemic activity of one or more inflammatory processes and/or components of innate or adaptive immunity in the absence of demonstrable cause, e.g., infection or tissue injury) and/or autoimmune diseases (generally involving immune response against a self tissue or tissue component, i.e., self-antigen, including a self antibody response or cell-mediated response, and also including organ-specific and non-organ specific autoimmune conditions. Preferably, such condition may be chosen from acute disseminated encephalomyelitis (ADEM); Addison's disease; Alzheimer's disease (AD); ankylosing spondylitis; antiphospholipid antibody syndrome (APS); aplastic anemia; atherosclerosis; autoimmune gastritis; autoimmune hepatitis; autoimmune thrombocytopenia; Behget's disease; coeliac disease; dermatomyositis; diabetes mellitus type I; diabetes mellitus type II; familial Mediterranean fever; familial cold-induced autoinflammatory syndrome; Goodpasture's syndrome; gout; pseudogout; Graves' disease; Guillain-Barré syndrome (GBS); Hashimoto's disease; hereditary periodic fevers; idiopathic thrombocytopenic purpura; inflammatory bowel disease (IBD) including Crohn's disease and ulcerative colitis; ischemia-reperfusion injury; Kawasaki's disease; mixed connective tissue disease; Muckle-Wells syndrome; multiple sclerosis (MS); myasthenia gravis; opsoclonus myoclonus syndrome (OMS); optic neuritis; Ord's thyroiditis; osteoarthritis; Parkinson's disease (PD); pemphigus; pernicious anaemia; polyarteritis nodosa; polymyositis; postoperative or traumatic inflammation; primary biliary cirrhosis; primary myoxedema; psoriasis; psoriatic arthritis; rheumatic fever; rheumatoid arthritis; Reiter's syndrome; scleroderma; Sjögren's syndrome; stroke-ischemia; systemic lupus erythematosus (SLE); systemic onset juvenile idiopathic arthritis; Takayasu's arteritis; temporal arteritis; vitiligo; warm autoimmune hemolytic anemia; and Wegener's granulomatosis.

Inflammation and inflammatory diseases and conditions, such as e.g. listed above, may constitute or give rise to inflammatory challenges that can—with differing susceptibility—lead to atherogenesis in patients.

More preferably, the present invention relates to diagnostic, prophylactic and/or therapeutic tools and/or methods particularly useful in conditions characterized by an altered status of the glycocalyx, such as an alteration of the glycocalyx width and/or the Capillary Volume Reserve. More preferably, the conditions are chosen from, but are not limited to, cancer, diabetes such as diabetes mellitus type I or diabetes mellitus type II, renal failure, premature arterosclerosis, sepsis, hypertension, malignant hypertension, pre-eclampsia Glycocalyx As used herein, "glycocalyx" generally refers to a polysaccharide-rich extracellular matrix on the luminal surface of vascular endothelial cells. Glycocalyx is primarily comprised of proteoglycans, glycosaminoglycans and glycoproteins (e.g., selectins, adhesion molecules, etc.) which associate in vivo with water and numerous molecules including inter alia plasma proteins, lipids and enzymes from the circulating blood.

The "status of the glycocalyx" refers to the condition of the glycocalyx at a particular point of time including the relative position. The status of the glycocalyx can be characterized by glycocalyx parameters. The term "alteration" with reference to glycocalyx parameters (e.g., volume or dimension, width, permeability, enzyme activity, etc.) generally encompasses any direction (e.g., increase or decrease) and extent of such alteration. For example, a "decrease" in a value of a parameter may include decreases by at least about 10%, or by at least about 20%, or by at least about 30%, or by at least about 40%, or by at least about 50%, or by at least about 60%, or by at least about 70%, or by at least about 80%, or by at least about 90%, compared to a relevant reference value, such as for example the value of said parameter in a control (healthy) subject. For example, an "increase" in a value of a parameter may include increases by at least about 10%, or by at least about 20%, or by at least about 40%, or by at least about 60%, or by at least about 80%, or by at least about 100%, or by at least about 150% or 200% or even by at least about 500% or like, compared to a relevant reference value, such as for example the value of said parameter in a control (healthy) subject. It will be appreciated that alteration of the glycocalyx parameters results in an alteration of the status of the glycocalyx.

More typically, a condition which involves glycocalyx degeneration may be characterised by decreased glycocalyx volume or dimension, increased glycocalyx permeability, increased shedding of glycocalyx (i.e., resulting in reduced thickness of the glycocalyx layer), increased activity of glycocalyx-degrading enzyme(s) and/or decreased activity of glycocalyx-synthesising enzyme(s). Desirably, a treatment intervention, such as, for example disclosed herein, would reverse these trends.

The term "enzyme of glycocalyx metabolism" generally encompasses enzymes which participate in the anabolism (i.e., formation) or catabolism (i.e., degradation) of glycocalyx or of one or more of its components. By preference, but without limitation, the term includes hyaluronidase, myeloperoxidase, heparinase and other exo- and endoglycosidases.

As noted, the above characteristics of endothelial glycocalyx may be advantageously determined by means of detecting one or more glycocalyx-related markers in a sample removed from a subject. In particular, such markers may include glycocalyx-derived molecules, glycocalyx-metabolism enzymes and/or endogenous or exogenous substances that can normally associate with glycocalyx.

Glycocalyx-derived molecules particularly suitable for detection herein include, without limitation, hyaluronan, heparan sulphate, dermatan sulphate, syndecan-1 and total plasma glycosaminoglycan (GAG) content. Commonly, such molecules may be released into bloodstream due to ongoing glycocalyx degradation or shedding, and can thus indicate degenerative alterations of glycocalyx.

Glycocalyx-metabolism enzymes particularly suitable for detection herein include, without limitation, hyaluronidase, myeloperoxidase, heparinase and other exo- and endoglycosidases. For example, increased or decreased circulating levels of such enzymes may indicate ongoing enzymatic reactions catalysed thereby, allowing to assess the glycocalyx homeostasis.

Endogenous and exogenous glycocalyx-associating substances particularly suitable for detection herein include, without limitation, glycocalyx permeating tracer molecules such as inter alia dextran 40, or endogenous lectin-like proteins which normally associate with glycocalyx. For example, the circulating amount of such substances, optionally following their injection or infusion, provide a representation of the capacity of glycocalyx to deplete said substances from the bloodstream and thereby an estimate of glycocalyx volume or dimension and molecular accessibility.

Biosensor

As mentioned, the invention also relates to a biosensor device configured to detect one or more glycocalyx-related markers, such as inter alia those defined above, in a sample removed from a subject; as well as to the use of said biosensor in the present diagnostic methods.

The term "biosensor" as used herein, generally refers to a device or apparatus that utilises one or more immobilised biologically-sensitive materials (such as, for example, a receptor, an antibody, an enzyme, a substrate, an organelle or a whole cell) to detect and/or quantify one or more desired analytes of interest in an analysed sample. A binding or chemical reaction between the immobilised biologically-sensitive material and said desired analyte is transduced into a detectable physical, chemical or physicochemical signal.

In a preferred embodiment, said immobilised biologically-sensitive material may be a receptor, such as without limitation a peptide, polypeptide, a protein, an antibody, an aptamer or a peptidomimetic, capable of specifically binding with a glycocalyx-derived molecule, a glycocalyx-metabolism enzyme or an endogenous or exogenous glycocalyx-associating substance as defined herein. Such binding may preferably display high affinity, i.e., having affinity constant ($K_A$) of $K_A \geq 1 \times 10^5$ $M^{-1}$, more preferably $K_A \geq 1 \times 10^6$ $M^{-1}$ such as, e.g., $K_A \geq 1 \times 10^7$ $M^{-1}$, yet more preferably $K_A \geq 1 \times 10^8$ $M^{-1}$, even more preferably $K_A \geq 1 \times 10^9$ $M^{-1}$, e.g., $K_A \geq 1 \times 10^{10}$ $M^{-1}$, $K_A \geq 1 \times 10^{11}$ $M^{-1}$, or $K_A \geq 1 \times 10^{12}$ $M^{-1}$, or even higher, wherein $K_A = [R\_A]/[R][A]$, R denotes the receptor and A denotes the desired analyte.

In a further preferred embodiment, said immobilised biologically-sensitive material may be a substrate capable of being acted upon and chemically altered by a glycocalyx-metabolism enzyme the detection of which is intended.

In yet another embodiment, said immobilised biologically-sensitive material may be an enzyme capable of acting upon and chemically altering a glycocalyx-derived molecule or an endogenous or exogenous glycocalyx-associating substance as defined herein.

The present invention contemplates any suitable manner of transducing the binding or reaction between the immobilised biologically-sensitive material and the desired analyte into a detectable signal and of detecting said signal.

In particular, the generated signal and the corresponding detector element of the present biosensor device may employ without limitation physicochemical, optical (e.g., using surface plasmon resonance, or based on absorbance or fluorescence changes), piezoelectric, electrochemical (e.g., to detect redox reactions using electrodes), thermometric, or magnetic modes of detection. The general design and use of biosensors is known in the art and can be applied for the uses of the present invention (see, e.g., Biosensors: A Practical Approach, 2nd ed., Cooper J and Cass T, eds., Oxford University Press 2003, ISBN 0199638462; and Biosensors: Theory and Applications, D G Buerk, Technomic Publishing Company 1993, ISBN 0877629757), incorporated specifically herein by reference.

Treatment

As further explained in the Summary section, the invention also contemplates treatment of vascular and inflammatory conditions or diseases, such as, for example, the respective diseases recited above, or treatment to reduce atherogenic susceptibility to inflammatory challenges, via glycocalyx constituents, or using inhibitors of enzymes of glycocalyx catabolism.

The terms "treat" or "treatment" encompass both the therapeutic treatment of an already developed disorder, such as the therapy of an already developed vascular or inflammatory disease, as well as prophylactic or preventative measures, wherein the aim is to prevent or lessen the chances of incidence of an undesired affliction, such as to prevent the chances of contraction and progression of a vascular or inflammatory disease. Beneficial or desired clinical results may include, without limitation, alleviation of one or more symptoms or one or more biological markers (e.g., of inflammatory cytokines, fever, atheromas, etc.), diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or disorder being treated. Methods are known in the art for determining therapeutically and prophylactically effective doses.

Glycocalyx constituents useful for prophylactic and/or therapeutic repair of glycocalyx in the above-defined disease states include by preference but without limitation, glycosaminoglycans; heparin including inter alia fractionated heparin; glycomimetics; substrates or intermediates of the hyaluronan synthesis pathway; and xylosides (which prime GAG synthesis).

Glycocalyx-catabolism enzymes useful as targets for inhibition in the treatment of the above-defined disease states include, by preference but without limitation, hyaluronidase, myeloperoxidase, heparinase and other exo- and endoglycosidases.

The term "inhibition" encompasses any extent of inhibition of a glycocalyx-catabolism enzyme, in particular of its glycocalyx-degrading enzymatic activity, such as, e.g., inhibition by at least about 10%, by at least about 20%, by at least about 30%, by at least about 40%, by at least about 50%, by at least about 60%, by at least about 70%, by at least about 80%, by at least about 90%, or even by about 100%, compared to activity of said enzyme in the absence of the inhibitor. The extent of such inhibition may be measured by assays known in the art.

The term "inhibitor" generally refers to a substance or molecule capable of achieving inhibition of a desired target, such as of a glycocalyx-catabolism enzyme.

The invention contemplates any type of inhibitor, such as including both reversible inhibitors, i.e., ones binding non-covalently to an enzyme and/or to an enzyme-substrate complex, as well as irreversible inhibitors, i.e., ones that covalently alter one or more amino acids usually in the active site of an enzyme. Among reversible inhibitors, the invention contemplates, without limitation, competitive inhibitors, non-competitive inhibitors, mixed-type inhibitors, partially competitive inhibitors and uncompetitive inhibitors.

Suitable types of inhibitors for use herein include, by preference but without limitation, a polypeptide or protein; an antibody, a peptide; a peptidomimetic; an aptamer; a chemical substance, preferably an organic molecule, more preferably a small organic molecule; a lipid; a carbohydrate; a nucleic acid, etc.

The terms "organic compound" or "organic molecule" as used herein refer to their broad connotation in the art. The terms encompass organic molecules which are natural products, as well as which are semi- or fully synthesised.

The term "small organic molecule", as used herein, refers to organic compounds with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

The term "antibody" is used herein in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments (including, e.g., Fab, Fab', F(ab')2, Fv and scFv fragments; diabodies; linear antibodies; single-chain antibody molecules) insofar they exhibit the desired biological activity (particularly, ability to specifically bind an antigen of interest), as well as multivalent and/or multi-specific composites of such fragments (e.g., dibodies, tribodies, and multibodies). The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

The term "aptamer" as used herein refers to single-stranded or double-stranded oligo-DNA, oligo-RNA or oligo-DNA/RNA or any analogue thereof that can specifically bind to a target molecule such as a protein or peptide, more typically to a peptide. Advantageously, aptamers can display fairly high specificity and affinity (e.g., $K_A$ in the order $1\times10^9$ $M^{-1}$) for their targets. Aptamer production is described, inter alia, in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated specifically by reference herein.

As used herein, the term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134), incorporated specifically by reference herein.

Pharmaceutical Formulations

For purposes of treatment of vascular and/or inflammatory diseases, the active substances of the present invention, such as in particular glycocalyx constituent(s) and/or inhibitor(s) of glycocalyx-catabolism enzymes may be advantageously formulated as pharmaceutical formulations.

Such pharmaceutical compositions typically comprise one or more active substances of the invention, or a pharmaceutically acceptable form thereof such as an N-oxide form, an addition salt, a prodrug, solvate or a stereochemically isomeric form thereof, and one or more pharmaceutically acceptable carrier/excipient.

The term "pharmaceutically acceptable salts" means pharmaceutically acceptable acid or base addition salts. The pharmaceutically acceptable acid or base addition salts are meant to comprise therapeutically active non-toxic acid and non-toxic base addition salt forms which the present active substances are able to form. The present active substances which have basic properties can be converted in their pharmaceutically acceptable acid addition salts by treating said base form with an appropriate acid. Appropriate acids comprise, for example, inorganic acids such as hydrohalic acids, e.g., hydrochloric or hydrobromic acid, sulphuric, nitric, phosphoric and the like acids; or organic acids such as, for example, acetic, propanoic, hydroxyacetic, lactic, pyruvic, oxalic, malonic, succinic butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. The present active substances which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine and the like.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions of the invention may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions of the invention can be, for example, systemic, local, tissue-specific, etc., depending of the specific needs of a given application of the invention.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be is suitably accomplished by uniformly and intimately blending together a suitable amount of the active substance in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the active ingredient with a solid carrier such as described above to provide a mixture having the necessary compression properties, and then compacting the mixture in a suitable machine to the shape and size desired. Moulded tablets maybe made by moulding in a suitable machine, a mixture of powdered active substance moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the active substances of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metered-dose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the active substance of the subject invention at a concentration of about 0.1 to 3.0 mg/ml.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The active substances and pharmaceutically acceptable salts thereof of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the active substances according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The present active substances may be used alone or in combination with any vascular disease or inflammatory disease therapies known in the art ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The dosage or amount of the present active substances used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 µg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks.

Size Distribution Method

In a further embodiment of the present invention, the inventors have determined a method for assessing the status of the glycocalyx. The status of the glycocalyx can be assessed using a size distribution method, wherein the endothelial glycocalyx dimension of individual capillary blood vessels or the Glycocalyx width (GW) is determined. Additionally, the size distribution method can also provide measurements for the width of red blood cells (RBCW) in the blood vessels, the vessel diameter (VD) and the Capillary Volume Reserve (CVR).

As used herein, "Red blood cell width (RBCW)" is defined as the average value of multiple measurements of the width of red blood cells at a microvascular segment of a blood vessel. Since the microvascular segment is characterized by only facilitating the perfusion of a single line of red blood cells (as shown in FIG. 4), measurements of the width of the single red blood cells can be performed.

As used herein, the "Vessel diameter (VD)" is defined as the diameter of the microvascular segment of the blood vessel perfused by a single line of red blood cells. The inventors have surprisingly found that during measurements of the RBCW a few percent of the red blood cells extend into the glycocalyx domain onto the luminal endothelial membrane from which red blood cells are excluded most of the time. Therefore the measurements of the RBCW also provide a number of measurement values that extend into the glycocalyx domain and therefore provide values for the vessel diameter. It has been shown that the measurements of the maximal value of multiple measurements of red blood cell width (RBCW) at a microvascular segment provide an accurate measurement of the vessel diameter (VD).

As used herein, the "Glycocalyx width (GW)" is the dimension of the gap between red blood cell width and vessel diameter. Since the glycocalyx width (GW) refers to the dimension of the endothelial glycocalyx of individual capillary blood vessels, it is indicative for the status of the glycocalyx.

As used herein, the "Capillary Volume Reserve (CVR)" is defined as the ratio of the second power of RBCWmax over the second power of the RBCW. The CVR can be defined according to the following formula:

$$CVR = \frac{RBCWmax^2}{RBCW^2},$$

with RBCWmax equal to VD for VD equal to or larger than the maximal width of single RBC.

In all other cases, RBCWmax is equal to the maximal width of single RBC.

Size distribution measurements can be performed on images obtained with clinical microscopes. In first instance, a blood vessel is visualized, and sequential images of the red blood cells perfusing the blood vessel are captured. For each image, the RBCW of the visualized red blood cells is measured and a size distribution is obtained. The measurement method measures at least 10, preferably more than 50, 100, 250, 500, 1000, 2500, 5000 or more RBCW values for a given blood vessel. The measurement of these values has revealed that a few percent of the red blood cells extend into the glycocalyx domain on the luminal endothelial membrane from which red blood cells are excluded most of the time. Therefore, the size distribution measurement provides a statistical distribution, wherein the majority of the measurements provide the actual RBCW value in the blood vessel, whereas only a few percent of the measurements provide a measurement of the actual vessel diameter. Therefore, the p50 value from the size distribution measurement(s) provides the actual mean RBCW value in the blood vessel, whereas the p99 value provides the maximal RBCW value corresponding to the value of the blood vessel diameter. As used herein, the term "p50 value" indicates that there is a 50% chance that the actual value may be below the presented value, and that there is a 50% chance that the actual value may be higher than the presented value. The "p50 value" therefore refers to the average RBCW value or corresponds to the median RBCW value. As used herein, the term "p99 value" indicates that there is a 99% chance that the actual value may be below the presented value, and that there is a 1% chance that the actual value may be higher than the presented value. The "p99 value" therefore corresponds to the maximal RBCW value and consequently to the vessel diameter.

As used herein the "average" value refers to the mean, median or mode value of the values as measured. The mean value, as used herein, refers to the arithmetic average of a data set. The median value, as used herein, refers to the number separating the higher half of a data set, from the lower half. The mode value, as used herein, refers to the value that occurs the most frequently in a data set.

From the measurements of the actual RBCW value and the vessel diameter, the glycocalyx width (GW) can be determined, since the glycocalyx width equals [the vessel diameter minus the actual RBCW value] divided by 2. By determining the glycocalyx width, the size distribution method provides the status of the glycocalyx.

The status of the glycocalyx can further be assessed by determining the CVR value according to the given formula. Since the CVR value provides both information regarding the vessel diameter and the glycocalyx width, this value can also be used for assessing the status of the glycocalyx. In cases where the glycocalyx width remains unchanged but the vessel diameter is reduced or enhanced, the CVR value, contrary to the glycocalyx width value, will provide an even more accurate information regarding the status of the glycocalyx.

Advantageous for this approach is that the present invention provides a strategy for determining the glycocalyx status without the need for identifying the exact position of the luminal surface of the vascular wall. Also it is not required to use the leukocyte-induced transient widening of RBC widths (see FIG. 4).

The measurement method of the present invention therefore allows an automated, non-invasive assessment of microvascular red blood cell width, the vessel diameter, the glycocalyx width, and the Capillary Volume Reserve in all imaged RBC perfused microvessels in clinical as well as experimental intravital microscopic recordings.

The term "non-invasive" as used herein refers to a procedure which does not penetrate mechanically, nor break, the skin. The procedure therefore does not require an incision into the body or the removal of biological tissue.

Additionally the inventors have found that only a few seconds of red blood cell perfusion are required in a given microvessel to allow analysis of red blood cell width, the vessel diameter, the glycocalyx width, and the Capillary Volume Reserve. Furthermore, all microvessels in a given field of view can be analyzed simultaneously and therefore the recording of a single field of view only takes seconds, and recording multiple fields of view can be accomplished within a matter of one or several minutes. The measurement method of the present invention therefore provides accurate distributions of red blood cell width, the vessel diameter, the glycocalyx width, and the Capillary Volume Reserve from more than 100 blood vessels in a short period of time.

More preferably, microvessel refers to a blood vessel with a small diameter, and preferably a diameter smaller than 100 µm, more preferably smaller than 50 µm, more preferably smaller than 25 µm, 20 µm, 19 µm, 18 µm, 17 µm, 16 µm, 15 µm, 14 µm, 13 µm, 12 µm, 11 µm, 10 µm, 9 µm, 8 µm, 7 µm, and more preferably smaller or equal to about 10 µm.

In a preferred embodiment, the present invention further relates to a method for assessing the status of the glycocalyx, comprising the steps of (a) measuring the width of Red Blood Cells (RBCW) in a blood vessel, preferably a micro-vessel;

(b) determining the glycocalyx width (GW) from the size distribution of the red blood cell width measurements, thereby assessing the status of the glycocalyx.

In a more preferred embodiment, the present invention further relates to a method for assessing the status of the glycocalyx, comprising the steps of (a) measuring the width of Red Blood Cells (RBCW) in a blood vessel, preferably a micro-vessel;

(a1) determining the size distribution of the measured RBCW (b) determining the glycocalyx width (GW) from the size distribution of the measured RBCW, thereby assessing the status of the glycocalyx.

Additionally, the size distribution of the measurements obtained in step (a) can further be used to determine the Capillary Volume Reserve.

According to the method of the present invention the Glycocalyx width can be defined as the (vessel diameter (VD) minus the red blood cell width (RBCW)) divided by 2.

The Capillary Volume Reserve can be defined as the ratio of the maximal vascular blood volume when glycocalyx volume is accessible to red blood cells, determined according to the following formula:

$$CVR = \frac{RBCWmax^2}{RBCW^2},$$

with RBCWmax equal to VD for VD equal to or larger than the maximal width of single RBC.

In all other cases, RBCWmax is equal to the maximal width of single RBC.

In another embodiment, the present invention relates to method for assessing the status of the glycocalyx, comprising the steps of:

(a) measuring the width of at least 10, preferably more than 50, 100, 250, 500, 1000, 2500 or 5000 Red Blood Cells in a blood vessel, preferably a micro-vessel; (b) repeating step (a) for at least 10, preferably more than 50, 100, 250, 500, 1000 blood vessels, preferably micro-vessels; and, (c) determining the glycocalyx width from the size distribution of the red blood cell width measurements, thereby assessing the status of the glycocalyx.

In yet another embodiment, the present invention relates to method for assessing the status of the glycocalyx, comprising the steps of: (a) measuring the width of at least 10, preferably more than 50, 100, 250, 500, 1000, 2500 or 5000 Red Blood Cells in a blood vessel, preferably a micro-vessel; (b) repeating step (a) for at least 10, preferably more than 50, 100, 250, 500, 1000 blood vessels, preferably micro-vessels; and, (b1) determining the size distribution of the measured RBCW (c) determining the glycocalyx width from the size distribution, thereby assessing the status of the glycocalyx.

In a further embodiment, the method of the present invention, additionally comprises the step of:

(d) determining the Capillary Volume Reserve from the size distribution of the red blood cell width measurements.

In another embodiment of the present invention the method for assessing the status of the glycocalyx, comprises the steps of:

(a) measuring the width of at least 10, preferably more than 50, 100, 250, 500, 1000, 2500 or 5000 Red Blood Cells in a first blood vessel, preferably a micro-vessel;

(b) repeating step (a) for at least 10, preferably more than 50, 100, 250, 500 or 1000 blood vessels, preferably micro-vessels;

(c) determining the maximal and median width value of the RBCs; and (d) determining the difference between the maximal and median width value; wherein said difference determines the glycocalyx width and assesses the status of the glycocalyx.

In another embodiment of the present invention, the inventors have found that the measurements can be performed in a matter of minutes and the method of the present invention therefore enables the detection of dynamic changes in the red blood cell width, vessel diameter, glycocalyx width, and Capillary Volume Reserve in response to a controlled stimulus.

Therefore the present invention provides a method for identifying compounds, cardiovascular risk factors, or lifestyle factors modulating the status of the glycocalyx, comprising the steps of:

(a) measuring the width of at least 10, preferably more than 50, 100, 250, 500, 1000, 2500, 5000 Red Blood Cells in a blood vessel in the presence and absence of said compound, cardiovascular risk factor, or lifestyle factor;

(b) repeating step (a) for at least 10, preferably more than 50, 100, 250, 500, 1000 blood vessels; and (c) assessing the status of the glycocalyx according to the method of the present invention, wherein a difference in the status of the glycocalyx in the presence and absence of said compound, cardiovascular risk factor, or lifestyle factor identifies said compound, cardiovascular risk factor, or lifestyle factor as modulating the status of the glycocalyx.

In a further embodiment, the present invention relates to a method for screening compounds, comprising the steps of:

(a) measuring the width of at least 10, preferably more than 50, 100, 250, 500, 1000, 2500, 5000 Red Blood Cells in a blood vessel, and preferably a micro-vessel, in the presence of at least one compound;

(b) repeating step (a) for at least 10, preferably more than 50, 100, 250, 500, 1000 blood vessels, preferably micro-vessels;

(c) repeating the measurements of step (a) and (b) for at least one other compound;

(d) repeating the measurements of step (a) and (b) in the absence of a compound, thereby establishing a control measurement; and, (e) assessing the status of the glycocalyx and determining the GW, and optionally the RBCW, VD, and CVR, in the presence and absence of said compounds;

wherein the status of the glycocalyx is assessed in relation to the used compounds and the control measurement, thereby screening said compounds for their ability to modulate the status of the glycocalyx.

In a further embodiment, the present invention relates to a method for identifying a compound, cardiovascular risk factor, or lifestyle factor to modulate the glycocalyx and/or Capillary Volume Reserve, said method comprising:

a) introducing into a computer program information defining the average width value of Red Blood Cells (RBCs) in at least one blood-vessel in the absence of said compound, cardiovascular risk factor, or lifestyle factor, b) introducing into a computer program information defining the average and maximal width value of RBCs in at least one blood-vessel in the presence of said compound, cardiovascular risk factor, or lifestyle factor, c) assessing whether the GW in the presence of said compound, cardiovascular risk factor, or lifestyle factor differs from the GW in the absence of said compound, cardiovascular risk factor, or lifestyle factor, and, d) identify compounds, cardiovascular risk factor, or lifestyle factor which are positively assessed in c).

According to the present invention the terms cardiovascular risk factor and lifestyle factor refer to one or more risk factors chosen from age, smoking, hyperglycaemia and dyslipidemia; and/or in subjects having one or more risk pathologies chosen from ischemia-reperfusion injury, type 1 diabetes, type 2 diabetes, hyperglycaemia, insulin resistance, metabolic syndrome, dyslipidemia, hypercholesterolemia, hypertri-glyceridemia, hypertension, cancer, infectious disease and trauma.

Accordingly, in an aspect the invention provides a method for diagnosing cancer or diabetes or the susceptible to cancer or diabetes in a subject, comprising detecting in said subject an alteration in the status of the glycocalyx. By means of example and not limitation, alterations in the status of the glycocalyx, in subjects diagnosed with cancer or diabetes, can be compared to control subject or subjects not diagnosed with cancer or diabetes or not susceptibility to cancer or diabetes, to assess whether a significant difference occurs that may be indicative of the pathological phenotype.

In other embodiments, some diagnostic methods may need to be carried out on the body of a subject. By means of example and not limitation, measuring the width of at least 10, preferably more than 50, 100, 250, 500, 1000, 2500, 5000 Red Blood Cells in a first blood vessel, and preferably a micro-vessel and repeating this measurement for at least 10, preferably more than 50, 100, 250, 500, 1000 blood vessels in human and other subjects by intravital microscopic recordings imaging, as shown in the examples.

It should be noted that this type of intravital microscopic recordings measurement technique is a simple and fast method for diagnosis, not requiring invasive microscopic visualisation techniques which comprise injection of fluorescent labels attached to glycocalyx-bound proteins or glycocalyx permeating tracer molecules.

It shall be appreciated that the above diagnostic methods and therapeutic interventions may be used in combination or synchrony, particularly to advantageously tailor treatment to individual patients. For instance, where a diagnostic assay as above determines that the status of the glycocalyx is significantly altered in a patient, the treatment in said patient may be subsequently aimed to restoring the status of the glycocalyx.

Also, the present diagnostic methods can be used to monitor, even in individual patients, the effectiveness of any therapeutic interventions in restoring the status of the glycocalyx (e.g., of treatments as disclosed herein; or other treatments, such as inter alia medication to improve insulin sensitivity in diabetic patients, heparin therapy in cancer patients, existing treatments designed to improve endothelial function in inflammatory diseases, etc.), with respect to status of the glycocalyx.

A further embodiment of the present invention relates to a computer program stored on a computer readable medium or similar standalone computer device configured to:
  (a) read the RBCW distribution data; and
  (b) determine the status of the glycocalyx according to the method of the present invention, thereby determining the GW, and optionally, the RBCW, VD and CVR.

In yet another embodiment, the present invention relates to a computer device comprising data comprising the average width value of the Red Blood Cells in at least one blood-vessel, obtained by using the methods according to the present invention.

In yet another embodiment, the present invention relates to a computer program comprising the code means adapted to perform the following steps, when said program is run or executed on a data processing system:
  (i) comprising the method steps of the present invention or
  (ii) the method steps for determining the GW, and optionally, the RBCW, VD and CVR from the RBCs width distribution data.

In yet another embodiment, the present invention relates to a computer program as described herein, wherein the size distribution data and GW, and optionally, the RBCW, VD and CVR values are compared to a standard value. Preferably, said standard value is obtained by retrieval from a database.

In yet another embodiment, the present invention relates to a method for identifying a compound to modulate the glycocalyx, said method comprising:
  (a) introducing into a computer program information defining the RBCW values in at least one blood-vessel in the absence of said compound,
  (b) introducing into a computer program information defining the RBCW values in at least one blood-vessel in the presence of said compound,
  (c) determining the status of the glycocalyx according to the method of the present invention,
  (d) assessing whether the status of the glycocalyx in the presence of said compound differs from the status of the glycocalyx in the absence of said compound, and,
  (e) identify compounds which are positively assessed in (d).

In yet another embodiment, the present invention relates to a method of operating a data-processing system:
  (i) comprising the method steps of the present invention or
  (ii) the method steps for determining the red blood cell width, vessel diameter, glycocalyx dimension, and/or Capillary Volume Reserve from the RBCW distribution data.

In yet another embodiment, the present invention relates to a data processing system comprising means to carry out the method steps of the present invention and/or the method steps for determining the red blood cell width, vessel diameter, glycocalyx dimension, and Capillary Volume Reserve step from the RBCs width distribution data.

In yet another embodiment, the present invention relates to a computer-readable medium on which are stored code means adapted to perform each of the steps of the method according to the present invention.

In yet another embodiment, the present invention relates to a computer device comprising data comprising red blood cell width, vessel diameter, glycocalyx dimension, Capillary Volume Reserve and/or RBCs width distribution data obtained by using the methods according to the present invention.

It should be noted that the device according to the present invention is capable of visualizing and determining the status of the glycocalyx for all kinds of animals, including mice, rats, hamsters, guinea pigs, rabbits, etc. but also in humans. The visualization can be performed on any part of the body where blood vessels can be visualized, and preferably on the tongue, ear, skin, nail fold, eye, etc.

The above aspects and embodiments are further supported by the following non-limiting examples.

EXAMPLES

Example 1

The present example demonstrate that endotoxin-induced inflammatory reactions lead to a decrease of glycocalyx volume or dimension in humans and that Tumour Necrosis Factor-$\alpha$ (TNF$\alpha$) plays a role in this process. In particular, healthy male volunteers received a low-dose endotoxin intravenously, with (n=8) or without (n=13) pre-treatment with the soluble TNF$\alpha$receptor Etanercept. Systemic and microvascular glycocalyx were estimated at baseline and 4 hours after endotoxin challenge:

Materials & methods
Study Design

Twentyone healthy Caucasian male volunteers were studied. The study was approved by the Institutional Review Board of the Academic Medical Centre, Amsterdam and written informed consent was obtained from all volunteers. Participants had no history of cardiovascular disease. Subjects did not smoke, did not use any medication and were free from any febrile illness in the month preceding the study. Medical history, physical examination, routine laboratory examination, electrocardiogram and chest X-ray were normal and comparable. All experiments were performed after an overnight fast. A baseline measurement comprising systemic glycocalyx volume, microvascular glycocalyx thickness and biochemistry was performed in all subjects. Five days later, subjects were allocated to intramuscular injection of either saline (n=13) or Etanercept (n=8; Enbrel® 50 mg, Wyeth Pharmaceuticals, Madison, N.J., USA). After 48 hours, all subjects received a bolus injection of endotoxin intravenously (1 ng/kg body weight), United States Pharmacopeial Convention Inc, Rockville, Md., USA). The incidence, time and severity of clinical symptoms associated with endotoxemia were recorded as previously published (Suffredini et al. 1999.

J Infect Dis 172: 1278-82). After the endotoxin infusion, vital signs including blood pressure, heart rate and body temperature were measured at regular intervals. Systemic glycocalyx volume and microvascular glycocalyx thickness were measured approximately 4 hours after endotoxin infusion, but at the same time of day as the baseline measurement.

Estimation of Systemic Glycocalyx Volume

Systemic glycocalyx volume was estimated as previously published by subtracting circulating plasma volume from the intravascular distribution volume of the glycocalyx permeable tracer Dextran 40 (Nieuwdorp M et al. 2006. Diabetes 55: 480-6; Suffredini et al. 1999, supra). Circulating plasma volume was calculated with a previously published method (Orth et al. 1998. Anesth Analg 87: 1234-8). The intravascular distribution volume of labelled autologous erythrocytes was used to quantify the circulating blood volume. Blood was drawn and centrifuged at 1,330 rpm for 5 minutes. Subsequently, sodium fluorescein (fluorescein-di-Na 25%, 250 mg/ml, AZUA Pharmacy, Amsterdam, the Netherlands) was added to the erythrocyte fraction for 5 minutes. After careful washing, labelled erythrocytes were resuspended in saline to the initial volume (60 ml) and re-infused. Subsequently, blood was drawn at 4, 5, 6, and 7 minutes after infusion. The fraction of labelled erythrocytes in the total erythrocyte pool was used to estimate the circulating erythrocyte volume ($V_{ERY}$). Pre-injection unlabeled erythrocytes served as negative control. The fraction of labelled erythrocytes in the blood was measured using a FACScan analyzer (FACS Calibur®, Becton Dickinson, Mountain View, USA). At least 100,000 cells were counted. Data were analyzed by Cellquest (Becton Dickinson, San Jose, Calif., USA). Haematocrit (Ht) was measured after centrifugation of heparinized blood in a Hettich-Haematokrit centrifuge at 10,000 rpm during 5 minutes (Hettich, Tuttlingen, Germany). Circulating plasma volume was calculated from $V_{ERY}$ and large vessel Ht by the following formula: circulating plasma volume=$([1-Ht] \times V_{ERY})$/Ht.

Dextran 40 (Rheomacrodex; NPBI International, Emmer-compascuum, the Netherlands) was used as a probe to estimate total intravascular volume, which includes the glycocalyx compartment. A bolus of 10 ml Dextran 1 (Promiten; NPBI International, Emmer-compascuum, the Netherlands) was injected to attenuate the risk of anaphylactic reactions prior to Dextran 40 infusion. 100 ml Dextran 40 was injected intravenously, followed by repeated blood sampling at 5, 7, 10, 15, 20, and 30 minutes. Dextran 40 concentration was calculated by measuring the increase in glucose concentration in the post infusion samples after hydrolyzation of Dextran 40 glucose polymers (Van Kreel et al. 1998. Clin Chim Acta 275: 71-80). Glucose concentration per time point was assessed in duplicate using the hexokinase method (Glucoquant, Hitachi 917; Hitachi). To determine the initial intravascular distribution volume of Dextran 40, the concentration of Dextran 40 at the time of injection was estimated by exponential fitting of the measured Dextran 40 concentrations. Exponential time constants ($\tau$ [min]) were used to determine Dextran 40 systemic clearance rates ($\tau^{-1}$ min$^{-1}$).

Estimation of Microvascular Glycocalyx

Thickness of endothelial glycocalyx in individual capillary blood vessels was measured by orthogonal polarization spectral (OPS) imaging of the sublingual microcirculation (Cytometrics, Philadelphia, Pa., USA) as previously published (Nieuwdorp et al. 2006, supra; Nieuwdorp et al. 2006. Diabetes 55: 1127-32). In short, the width of flowing erythrocytes was measured in 5 individual capillaries before and immediately after capillary leukocyte passage. In healthy capillaries, the glycocalyx limits capillary blood filling by separating erythrocytes from the luminal endothelial surface, which is known as the red cell exclusion zone. Under steady-state conditions, this red cell exclusion zone represents an upper bound on the maximum possible thickness of the endothelial glycocalyx. Since leukocytes transiently compress the capillary endothelial glycocalyx, the corresponding transient widening of the capillary erythrocytes column can be used to estimate capillary glycocalyx dimension (Han et al. 2006. Journal of Fluid Mechanics 554: 217-35). Images sized 728× 576 pixels were recorded were collected with a 5× objective providing a 325× magnification at a frame rate of 25/second. Analysis of the images was performed with Image Pro Plus (Media Cybernetics, Silverspring, Md., USA) by one single observer, who was blinded for clinical details of the participants. The anatomical capillary diameter and the width of the flowing erythrocyte column were measured using digital calipers prior to and after spontaneous capillary leukocyte passage. Per participant, glycocalyx dimension was determined in at least 5 capillaries. The mean of these results was calculated and used in further analyses. In addition as indication of capillary density, the number of capillaries per field was counted.

Blood Sampling and Laboratory Methods

Blood samples were drawn from the subjects at the baseline measurement, as well as at t=0, and ½1, 3, 4 and 24 hours after endotoxin infusion. After centrifugation, aliquots were snap-frozen in liquid nitrogen and stored at −80° C. Leukocyte plasma concentrations as well as subfractions were determined in EDTA plasma with standardized flow cytometric analysis. Plasma CRP levels were measured with a commercially available assay (Roche, Switzerland). Plasma soluble TNFα receptor type 2 (sTNFR2) levels were measured using an enzyme-linked immunosorbent assay (ELISA) (R&D Systems Inc, Minneapolis, Minn., USA), as a marker of effective Etanercept administration. Plasma IL-6 levels, a cytokine induced by TNFα activity, were measured using Cytometric Bead Array technique (R&D systems, Minneapolis, Minn., USA). Prothrombin activation fragment F1+2 (Dade Behring, Marburg, Germany) was measured by ELISA to estimate thrombin generation. D-dimer levels were measured as a reflection of fibrin formation and subsequent endogenous fibrinolysis with an automated quantitative latex-particle immunoassay (Biomerieux, Durham, N.C., USA). Quantitative plasma hyaluronan was measured by ELISA (Echelon Biosciences, Salt Lake City, Utah, USA), which measures total amount (including low and high molecular weight) hyaluronan. Heparan sulphate was measured after serum pre-treatment with Actinase E (Sigma, St. Louis, Mo., USA) by ELISA (Seikagaku Corporation, Tokyo, Japan). Total plasma hyaluronidase activity was determined with a previously published assay with minor modifications (24). In short, CovaLink plates (Nunc, Wiesbaden, Germany) were coated with biotinylated hyaluronan (0.2 mg/mL, HyluMed® Sterile IUO Sodium hyaluronate, Genzyme Corp, Cambridge, Mass., USA). Plasma samples were diluted 800× and added to the plates for 2.5 hours at 37° C. at pH 3.7. Bovine hyaluronidase (Sigma, St. Louis, Mo., USA) was used for the standard curve. The remaining amount of hyaluronan was determined by binding of avidin-biotin complex (Vectastain, Vector Laboratories, Burlingame, Calif., USA), followed by addition of o-phenylenediamine (OPD) and 30% $H_2O_2$. Plates were measured in a reader at OD 492 nm.

Monocyte Flow Cytometry Procedure

Whole blood samples were collected in pyrogen-free lithium-heparin tubes and then incubated for 10 min with 9 volumes ice-cold erythrocyte lysis buffer and centrifuged for 10 min at 4° C. Remaining cells were washed twice with ice-cold PBS. For flow cytometric analysis $0.5 \times 10^6$ cells were incubated in FACS buffer mixed with antibody. All reagents were titrated to obtain optimal results as recommended by the manufacturers. Cell surface staining was performed with Fluorescein Isothiocyanate (FITC) labelled mouse anti-human CD14 (IgG2a), anti-human Allophycocyanin (APC) labelled CD18 (IgG1) and Phycoerythrin (PE) labelled anti-human CD11b (IgG1) and CD62L (IgG1) (R&D Systems, San Jose, Calif., USA). Appropriate isotype control antibodies were used to correct for non-specific antibody binding. After staining, the cells were washed, fixed in 4% paraformaldehyde, and analyzed by flow cytometry using a FACS Calibur flow cytometer. Data were analyzed with CellQuest software (Becton Dickinson, Franklin Lakes, N.J., USA).

Statistical Analysis

All values are provided as means±SEM. Differences in baseline characteristics between the endotoxin-saline and the endotoxin-Etanercept group were analyzed by independent-samples T-test. Changes within treatment groups were analyzed by one-way analysis of variance. Changes between treatment groups were analyzed by two-way analysis of variance (interaction treatment and time). Correlations between systemic glycocalyx volume and other parameters were calculated with the Spearman's rank correlation test (two tailed). $P<0.05$ was considered to represent a statistically significant difference.

Results

Clinical Responses to Endotoxin Infusion with or without Etanercept Pre-Treatment Prior to endotoxin infusion, no differences in clinical characteristics were observed between the saline and the Etanercept group. Infusion of endotoxin and systemic glycocalyx volume measurements were well tolerated and no serious adverse effects were encountered. Endotoxin infusion caused characteristic clinical symptoms, such as chills, headache, myalgia and nausea. These symptoms were transient in both groups, but occurred more frequently and more intensive in the saline group compared to the Etanercept group (data not shown). sTNFR2 levels were significantly increased after Etanercept pre-treatment (from 1.8±0.2 to 520±34 ng/mL, $p<0.0001$), indicating that Etanercept was effectively administered. Plasma levels remained elevated 4 hours after endotoxin infusion in the Etanercept group (646±83 ng/mL), whereas sTNFR2 plasma levels were only slightly affected in the saline group (from 2.1±0.3 to 5.2±0.5 ng/mL 4 hours after endotoxin, $p<0.01$). Blood pressure, heart rate and body temperature significantly changed 4 hours after endotoxin infusion in the saline group (systolic blood pressure: from 127±11 to 119±5 mmHg, ns; diastolic blood pressure: from 67±8 to 51±9 mmHg, $p<0.01$; heart rate: from 59±6 to 82±5, $p<0.01$; and body temperature: from 36.6±0.5 to 38.3±0.4° C., $p<0.01$ compared to baseline for all parameters). Etanercept attenuated these changes (systolic blood pressure: from 125±7 to 123±10 mmHg, ns; diastolic blood pressure: from 69±6 to 67±6 mm Hg, ns, heart rate: from 62±4 to 69±3, ns; and body temperature: from 36.6±0.5 to 37.3±0.5° C., ns compared to baseline for all parameters).

Etanercept Attenuated Endotoxin-Induced Glycocalyx Perturbation

Baseline systemic glycocalyx volumes were comparable between the two groups (saline group: 1.6±0.6 versus Etanercept group: 1.7±0.5 liters, ns). Systemic glycocalyx volumes were significantly reduced after endotoxin infusion in the saline group (to 0.8±0.4 liters, $p<0.01$), predominantly due to a reduction in Dextran 40 distribution volume (4.7±0.6 to 4.1±0.9 liters, $p<0.05$, see FIGS. 1A AND 1B). Circulating plasma volumes (3.1±0.4 to 3.3±0.7 liters, $p<0.05$) increased accompanied by a small drop in hematocrit values (0.44±0.03 to 0.41±0.03%, $p<0.01$). In addition, endotoxin resulted in a twofold increase of the systemic clearance rate ($\tau$—1) of Dextran 40 (from 0.008±0.005 to 0.015±0.008 min-1, $p<0.01$). Etanercept attenuated endotoxin-induced glycocalyx volume loss (to 1.1±0.2 liters, $p<0.01$) based on a reduction in Dextran 40 distribution volume (4.6±0.6 to 3.9±0.5 liters, $p<0.05$) without affecting circulating plasma volume (2.9±0.5 to 2.8±0.6 liters, ns), haematocrit values (0.43±0.02 to 0.42±0.02%, ns) or systemic Dextran 40 clearance rate (0.009±0.002 to 0.009±0.001 min-1, ns).

Figure 1:
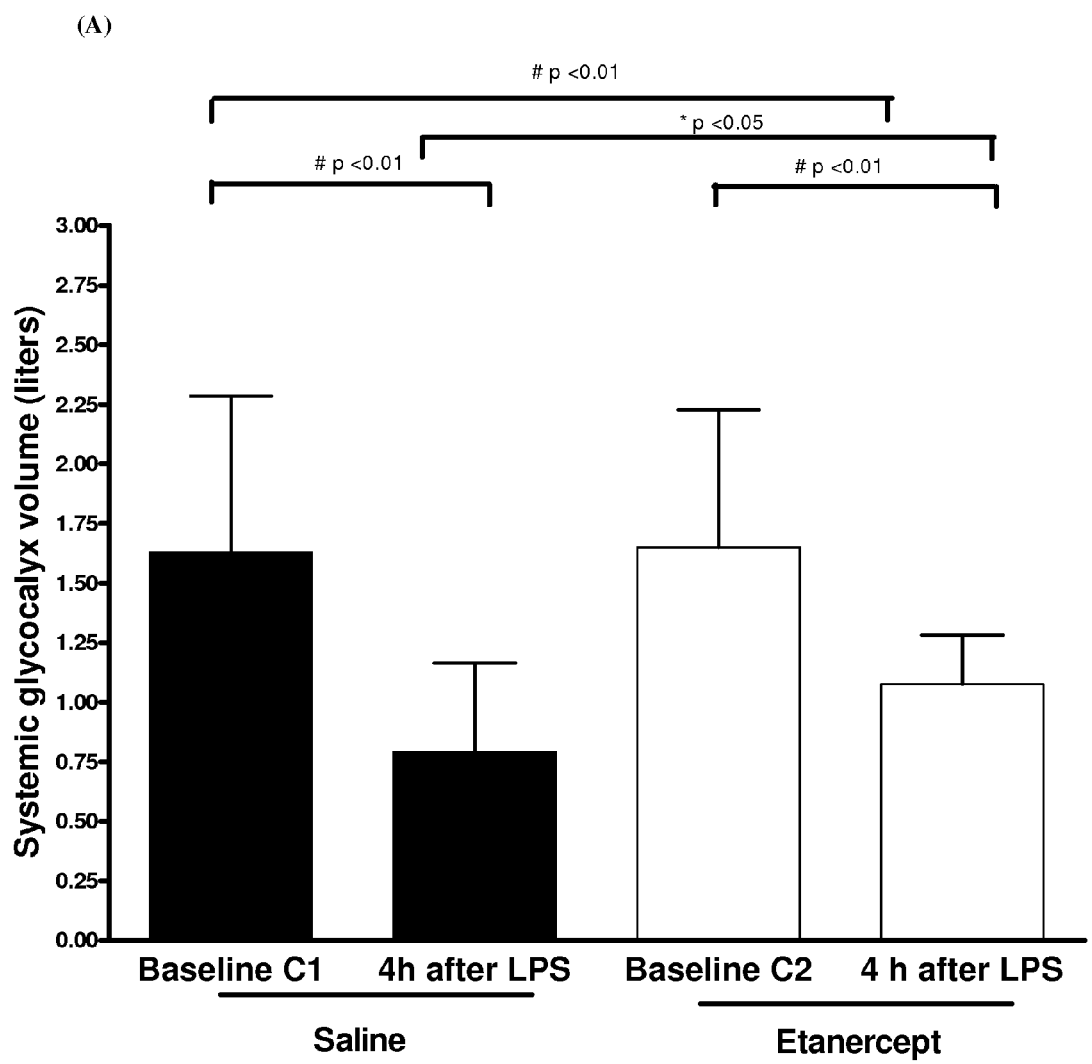
FIG. 1A. Systemic glycocalyx volumes were determined before and after endotoxin challenge without or with Etanercept pre-treatment. Data are presented as mean±SEM, *$p<0.05$, #$p<0.01$.
FIG. 1B. Plasma Dextran 40 clearance curves under baseline (open diamonds; closed diamonds), in the saline (closed squares) and Etanercept group (open squares). 4 hours after endotoxin infusion the rate of Dextran 40 plasma clearance was increased in the saline group as compared with Etanercept group. Depicted values on each time point are expressed as mean±SEM.
FIGS. 1C and 1D illustrate the effect of LPS (endotoxin) on glycocalyx dimension as determined by direct imaging of individual sublingual capillaries. Capillary glycocalyx dimensions were determined before (1C) and after (1D) endotoxin challenge. X-axis shows capillary glycocalyx dimension (in microns).
Figure 1:
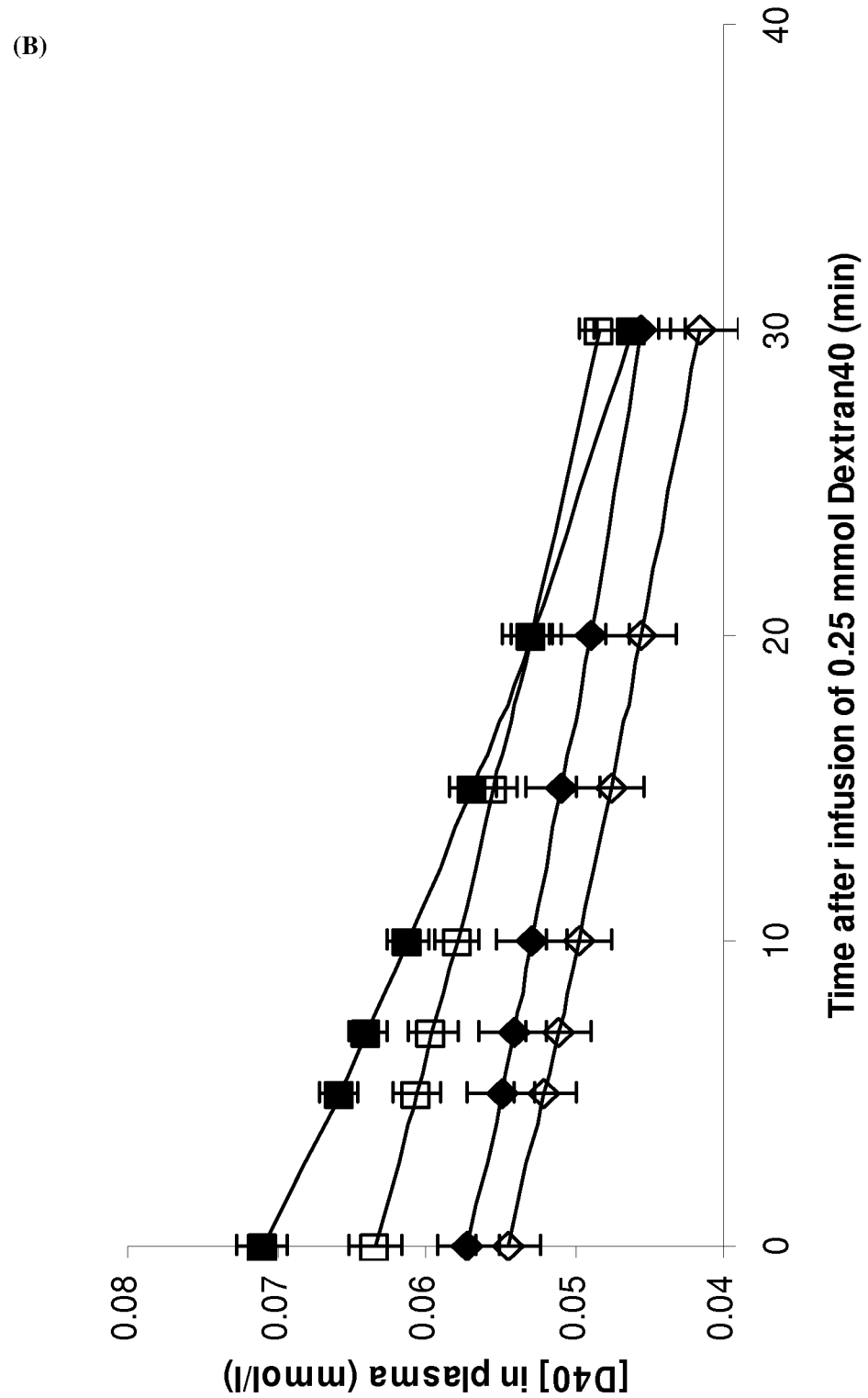
Figure 1:
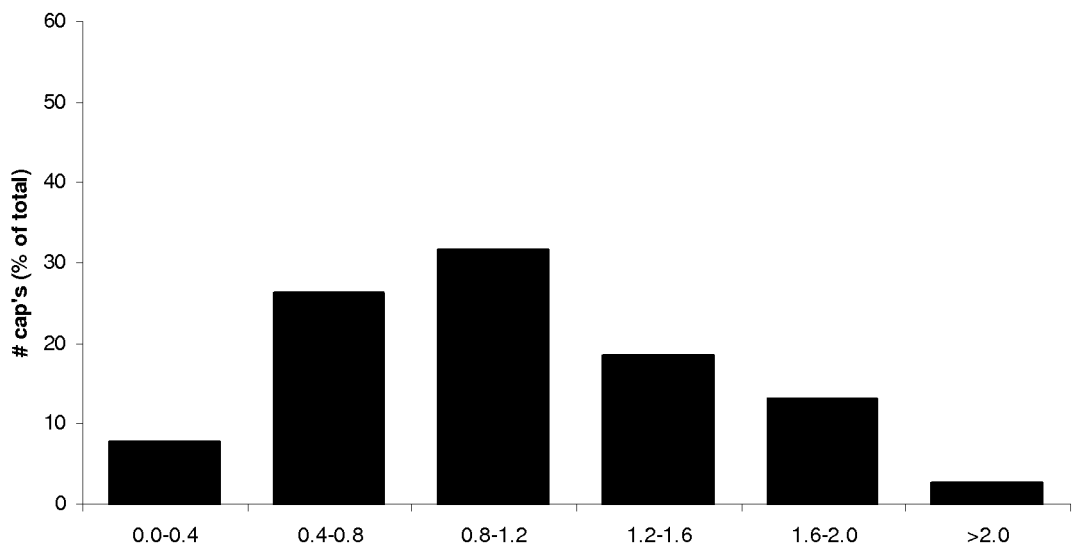
Figure 1:
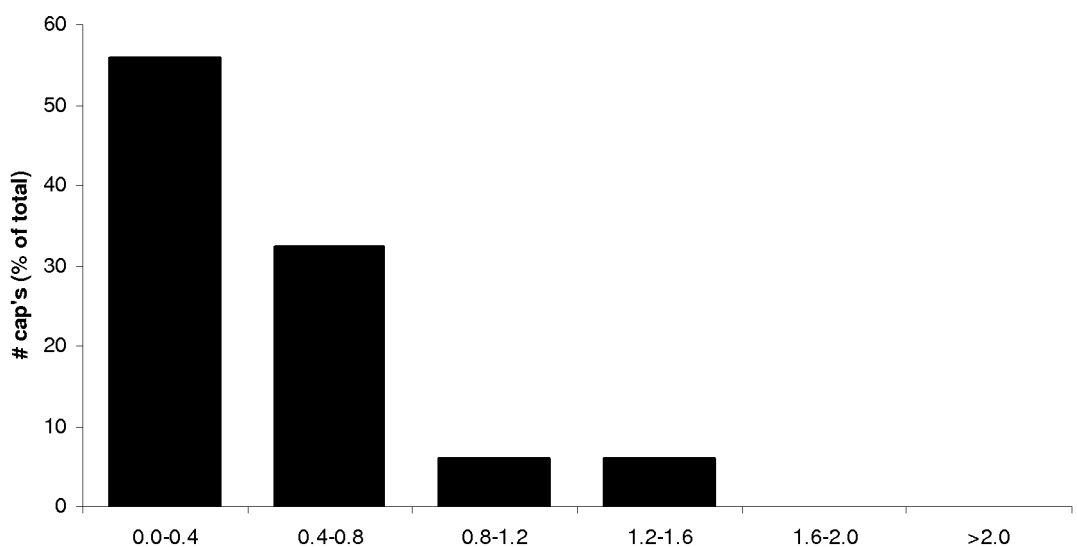

With regard to microvascular glycocalyx, endotoxin infusion led to a reduction in median microvascular glycocalyx thickness in the saline group (from 1.1 to 0.4 μm, $p<0.01$, see FIGS. 1C AND 1D). Loss of glycocalyx resulted in a slightly increased capillary blood filling as reflected by an increased width of the capillary erythrocyte column (from 4.9±0.2 to 5.3±0.3 μm, ns) prior to leukocyte passage. In addition, loss of glycocalyx was accompagnied by a reduction in anatomic capillary diameters (from 7.0±0.2 to 6.2±0.3 μm, $p<0.05$). Capillary density significantly decreased upon endotoxin challenge (from 60±18 per field to 44±16, $p<0.01$) with similar changes in the Etanercept pre-treatment group (from 59±7 to 43±15, $p<0.01$).

Changes in Glycocalyx Components Upon Endotoxin Infusion

Figure 2:
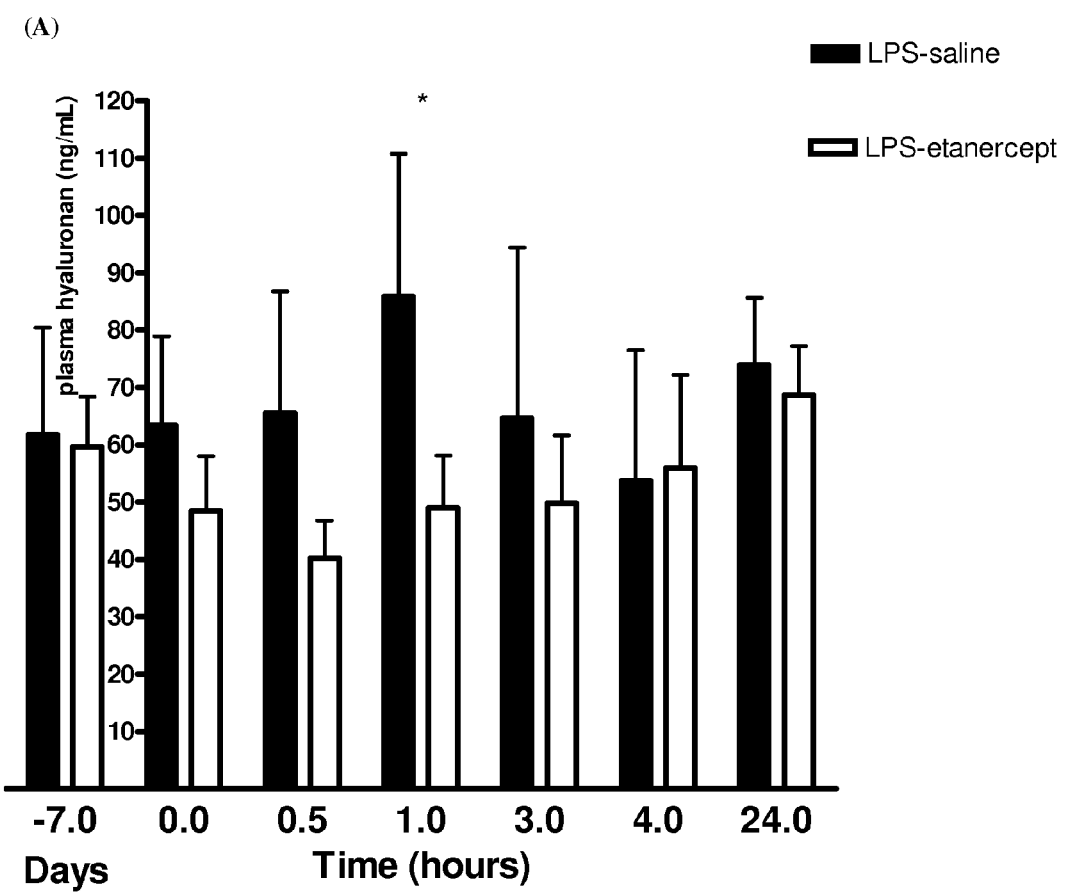
FIG. 2. Plasma hyaluronan levels (FIG. 2A) and hyaluronidase activity (FIG. 2b) in human volunteers challenged with endotoxin without (dots) or with Etanercept pre-treatment (diamonds). Data are presented as means±SEM (*$p<0.05$ vs. baseline, # $p<0.05$ between groups).
Figure 2:
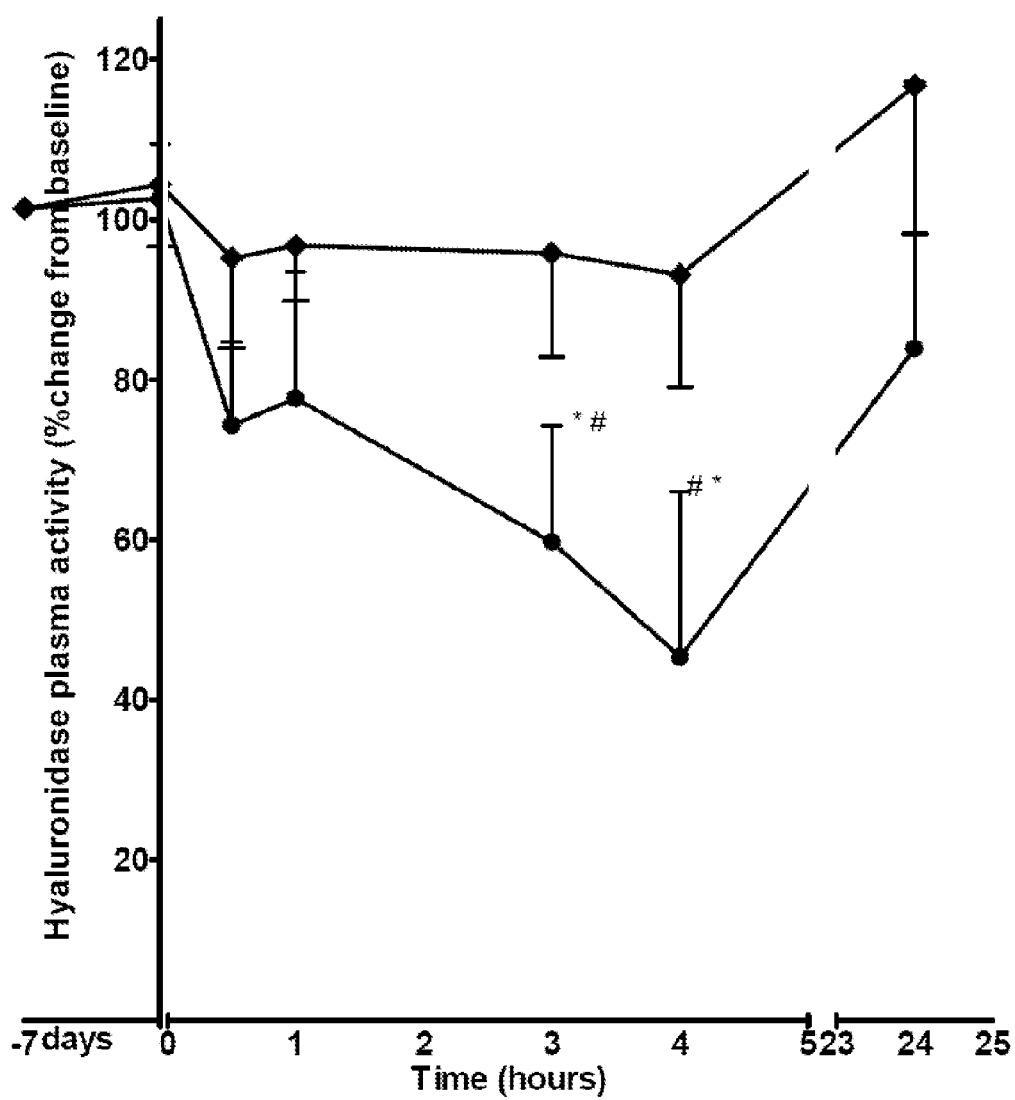

Plasma hyaluronan levels, a marker of glycocalyx shedding, rose significantly within first hour after endotoxin infusion in the saline group (from 62±18 to 85±24 ng/mL, $p<0.05$), whereas Etanercept reduced endotoxin-induced shedding (from 58±13 to 46±10 ng/mL, $p<0.05$) (FIG. 2A). Plasma hyaluronidase activity was significantly decreased 4 hours after endotoxin infusion in the saline group (−56±20% compared to baseline, $p<0.01$), whereas hyaluronidase activity was not affected in the Etanercept group (−8±14% compared to baseline, ns; FIG. 2B). Notably, heparan sulphate plasma levels did not significantly change during the 4 hours after endotoxin challenge with either pre-treatment (saline group: from 5.3±1.1 to 5.5±1.2 μg/mL versus Etanercept group: from 5.4±1.3 to 5.1±1.0 μg/mL, ns compared to baseline). However, 24 hours after endotoxin infusion plasma heparan sulphate levels increased more in the saline group (11.2±2.1 μg/mL versus Etanercept group 7.4±1.5 μg/mL, $p<0.01$).

Figure 3:
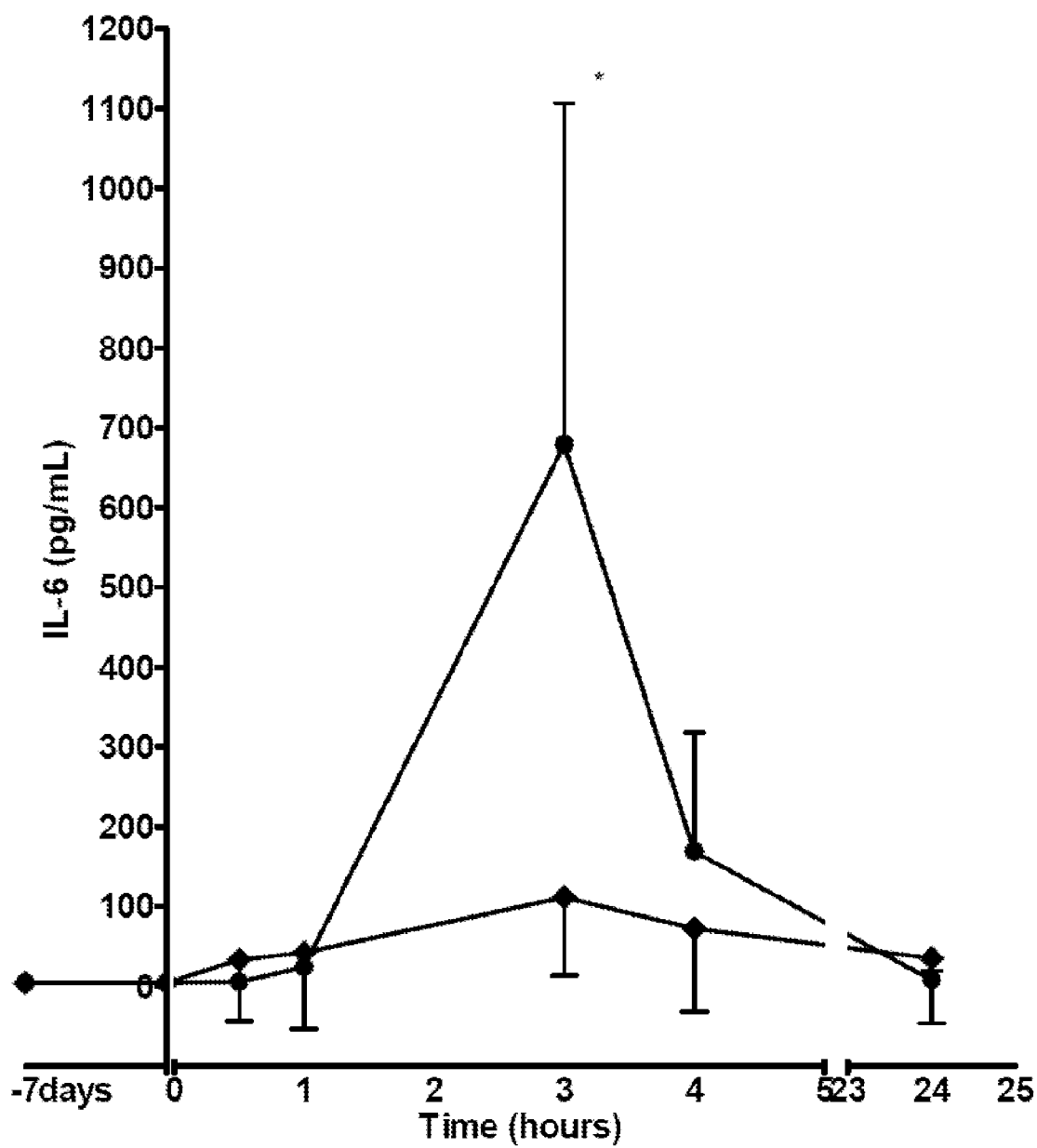
FIG. 3. Markers of inflammation were assessed by plasma IL-6 levels (FIG. 3A, without (dots) or with (diamonds) Etanercept pre-treatment) and plasma CRP plasma levels (FIG. 3B, without (black bars) and with (white bars) Etanercept pre-treatment) during endotoxin challenge in human volunteers. Activation of coagulation (FIG. 3C, as assessed by prothrombin fragments 1+2) and fibrinolysis (FIG. 3D, determined by D-dimer levels) parameters are depicted; (dots.
Figure 3:
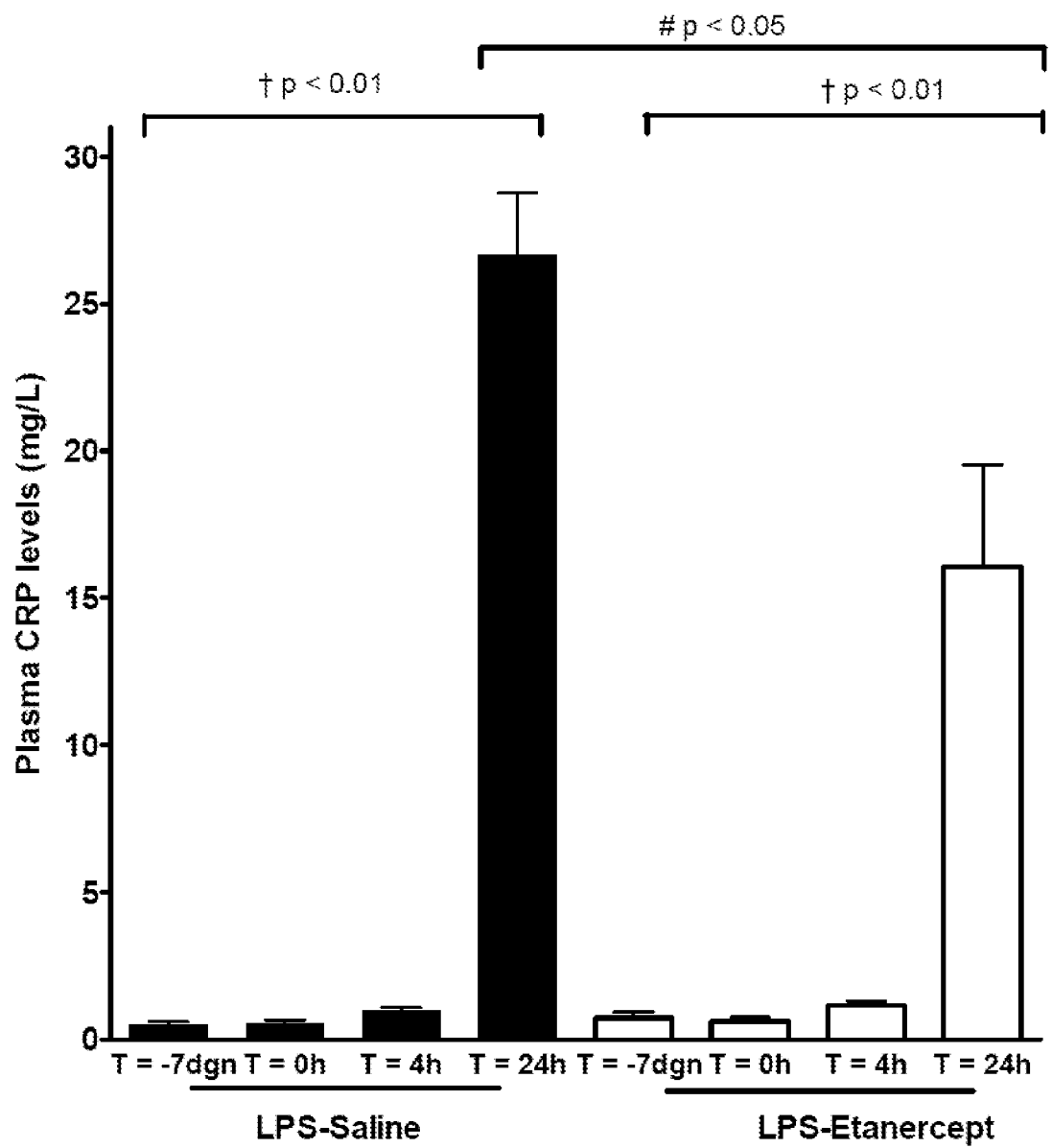
Figure 3:
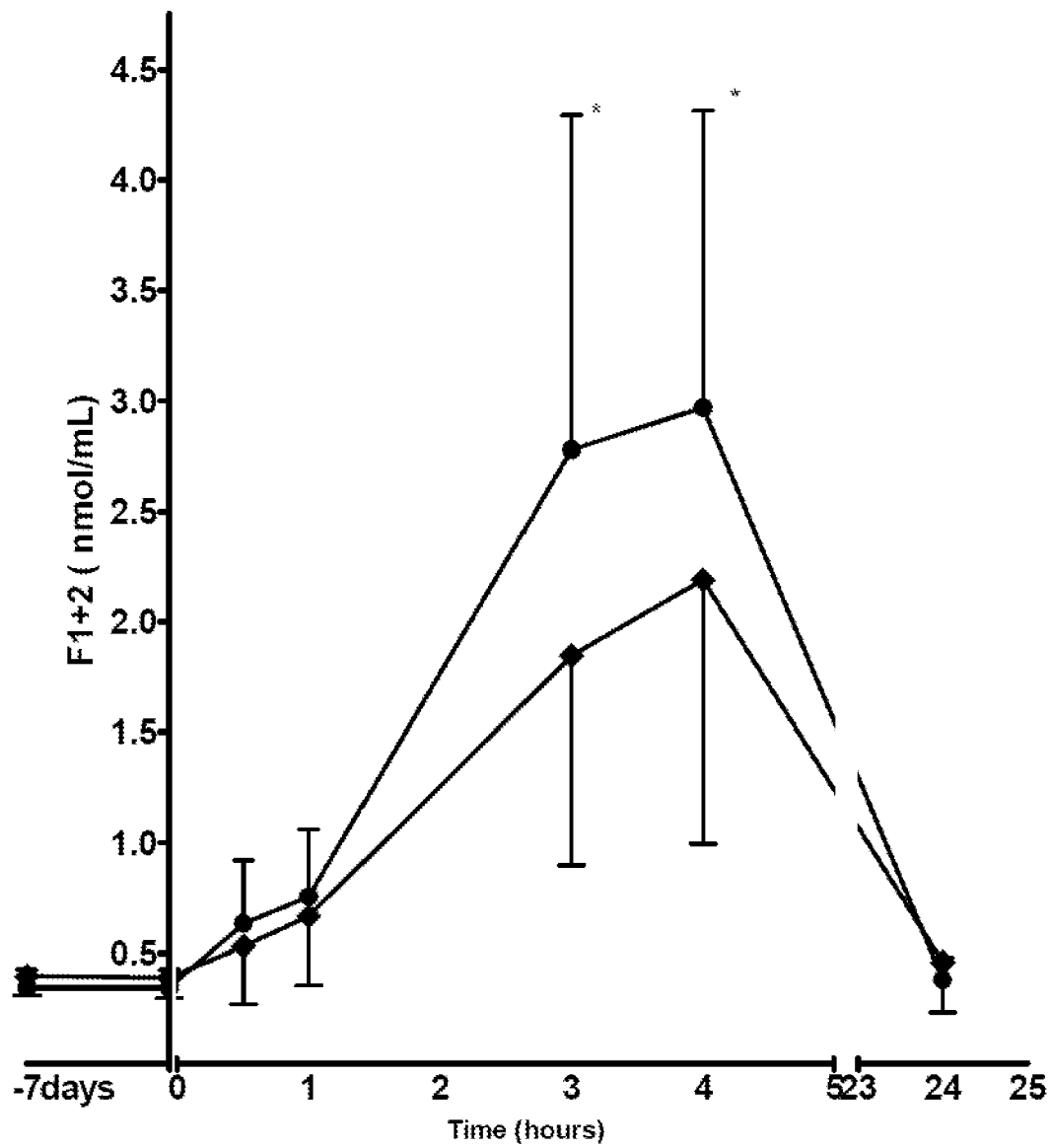
Figure 3:
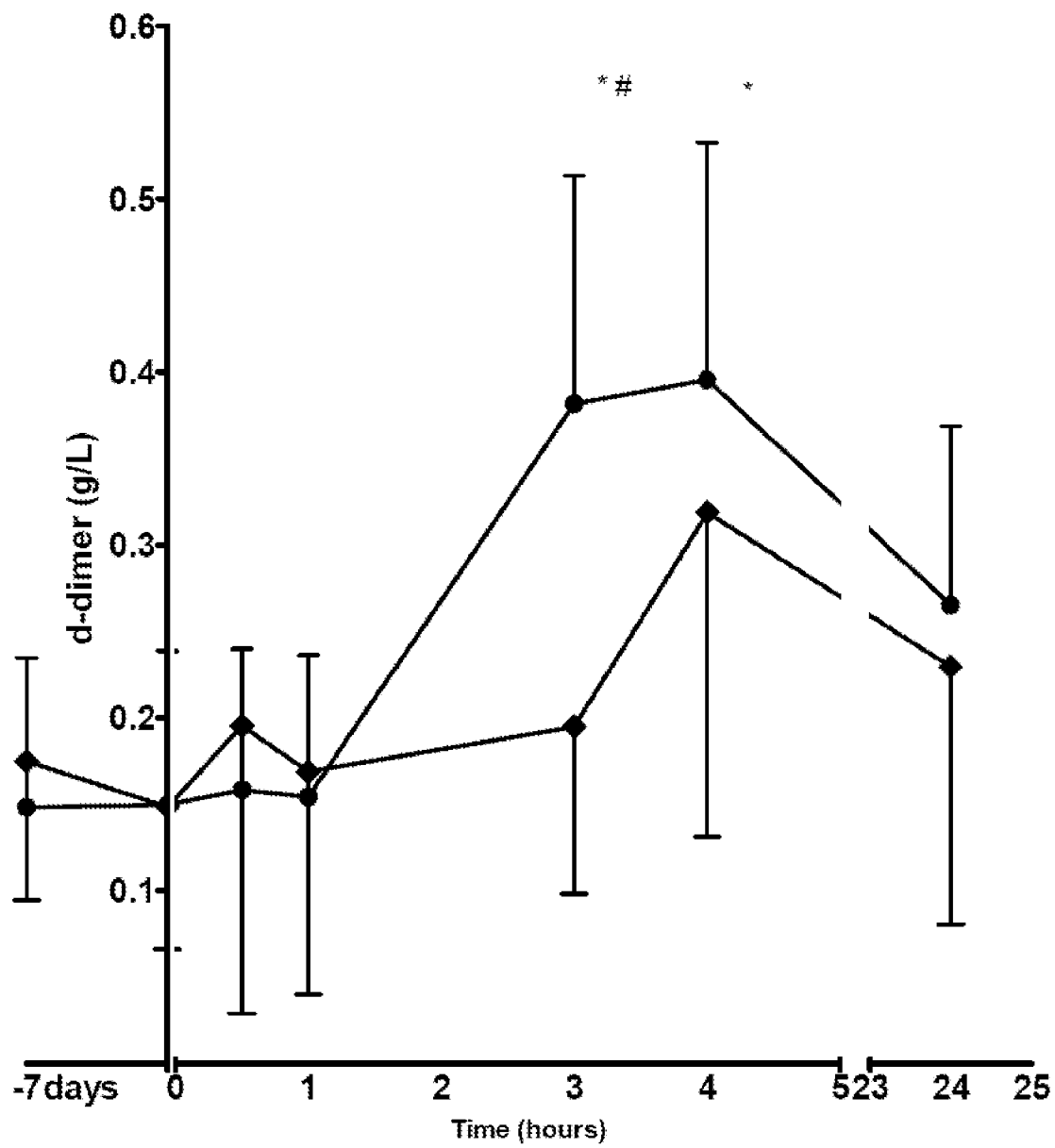

Etanercept Treatment Reduced TNFα-Induced Inflammatory and Coagulation Responses Inflammatory markers rose in the saline group after endotoxin challenge (IL-6: from 4.2±6.3 to 678±427 μg/mL and CRP: from 0.5±0.4 to 26.7±7.6 mg/L, $p<0.01$ compared to baseline, see FIGS. 3A AND 3B). Etanercept significantly reduced this increase (IL-6: from 4.6±3.1 to 127±98 μg/mL, $p<0.05$ compared to baseline and CRP: from 0.6±0.4 to 16.0±3.4 mg/L, $p<0.01$ compared to baseline, FIGS. 3A AND 3B). In parallel, 4 hours after endotoxin, the number of circulating leukocytes was doubled in both treatment groups compared to baseline.

With respect to leukocyte differentiation after endotoxin infusion, a significant drop in monocyte count by 76±29% was observed in the saline group at 4 hours ($p<0.01$ compared to baseline), whereas Etanercept was associated with a less profound reduction of 51±32% ($p<0.05$ compared to baseline). There was no difference between $CD14^+$ monocyte counts between the two groups (27±10 versus 26±13%, ns). However, the $CD11b^+/CD18^+$ (Mac-1 complex) monocyte count was higher after saline compared to Etanercept (median 0.82±0.2 versus 0.65±0.1, $p<0.01$). Finally the percentage of $CD62L^+$ (L-selectin) expressing monocytes was decreased at maximum 4 hours after endotoxin in the saline group whereas in the Etanercept group an increase was observed (—8±37% vs.+66±42%, p<0.05).

In parallel, markers of endotoxin-induced thrombin generation and subsequent fibrinolysis in saline group were significantly increased, starting 3 hours after endotoxin challenge (F1+2: from 0.3±0.1 to 2.8±1.5 nmol/L and D-dimer: from 0.2±0.1 to 0.4±0.1 mg/L, p<0.05 compared to baseline; FIGS. 3C AND 3D), whereas Etanercept significantly reduced this increase (F1+2: from 0.3±0.1 to 2.1±0.9 nmol/L, and D-dimer: from 0.2±0.1 to 0.3±0.1 mg/L, p<0.05). When data at baseline and 4 hours after endotoxin infusion were pooled for both groups, an inverse correlation was present between systemic glycocalyx volume and F1+2 or D-dimer levels (r=−0.74 and r=−0.60 respectively, both p<0.01).

CONCLUSIONS

These data demonstrates that inflammatory activity in part mediated by TNFα. leads to perturbation of the endothelial glycocalyx. This mechanism contributes to the inflammation-induced increase in vascular vulnerability. In line with the present data, the invention provides diagnostic and therapeutic approaches to inflammatory and vascular diseases, involving the detection and modulation of glycocalyx health.

Example 2

The present example provides a comparative example between the method of the present invention and two prior art methods. The method of the invention is compared to (1) the prior art method wherein leukocyte-induced transient widening of RBC widths is used and (2) the prior art method wherein the status of the glycocoalyx is assessed using tracers (cf FIG. 4).

The method of the invention (FIGS. 4A and 4C) measures the status of the endothelial glycocalyx (2) in individual capillary blood vessels (1) perfused with Red Blood Cells (3) by performing size distribution measurements determining the Red blood cell width (RBCW), the Vessel diameter (VD), the Capillary Volume Reserve and the Glycocalyx width (GW). For a single measurement to take place, the blood vessels require a visualisation of 5 seconds, wherein more than 100 RBCW measurements are performed in at least 10 blood vessels. The number of measurements can be increased in at least 10-fold by visualizing for about 1 minute. The size distribution of the measured RBCW values enables the precise assessment of the status of the glycocalyx.

2.1 Leukocyte-Induced Transient Widening of RBC Width

The prior art method based on leukocyte-induced transient widening of RBC widths (FIG. 4B) measures about 2 leukocytes per measurement in all visualised blood vessels and therefore requires a visualization time of at least 10 minutes before enough data is gathered to determine the status of the glycocalyx. Furthermore, it is noted that this type of measurement can only be performed on blood vessels that allow the, be it rare, passage of leukocytes (4). For small blood vessels such as microvessels extremely long visualisation times are required.

First, the data for the glycocalyx width obtained with this method are comparable to the measurements performed with the method of the present invention. Nevertheless, it is noted that the error margins are smaller, i.e. percent confidence level is higher, with the data of the present invention relative to the prior art method. This can be explained by the differences in width of the individual leukocytes.

Second, the data are obtained 10-100 times faster with the method of the present invention compared to the prior art method based on leukocyte-induced transient widening of RBC width.

2.2 Tracer Method

Prior art measurements of the status of the glycocalyx are performed using the addition of tracers into the blood stream. This method requires taking blood from a patient, marking the blood outside the patient and injecting the marked blood into the patient. After several hours, usually 4, blood is extracted from the patient and analysed. This analysis provides information regarding the status of the glycocalyx.

Compared to the Method of the Present Invention:

(1) this prior art method is very labour intensive and takes a long time;

(2) this prior art method is very unpleasant to patients. In fact some patients develop an allergic reaction to the tracers, putting the life of the patient at risk.

(3) Further, since the smaller blood vessels only allow a limited perfusion by red blood cells, this prior art method provides only one measurement of the status of the glycocalyx which may not be accurate.

Example 3

The present example demonstrates that by establishing the status of the glycocalyx according to the method of the present invention enables the fast detection of changes in the status of the glycocalyx.

Materials & Methods

The status of the endothelial glycocalyx in individual capillary blood vessels was measured by performing size distribution measurements thereby determining the Red blood cell width (RBCW), the Vessel diameter (VD), the Capillary Volume Reserve and the Glycocalyx width (GW). Clinical sublingual videomicroscopic images were obtained using a MicroScan Video Microscope System (MicroVision Medical, The Netherlands). The System is a handheld video microscope with LED illumination equipped with 5× magnification. For improved assessment of red blood cell velocity, stroboscopic illumination is introduced. The System has a standard video-output (PAL or NTSC) which is connected to an AD capture device to convert the images into a digital signal which is recorded directly to a computer harddrive.

The Red blood cell width (RBCW) is presented here as the median value of multiple measurements of red blood cell width at a microvascular segment that facilitates single file red blood cell perfusion. The Vessel diameter (VD) is the maximal value or p99 value of multiple measurements of red blood cell width at a microvascular segment that facilitates single red blood cell perfusion and the Glycocalyx width is the dimension of the gap between red blood cell width and vessel diameter. The Capillary Volume Reserve (CVR) is the ratio of (VD)^2 over (RBCW)^2.

The status of the glycocalyx was determined by performing size distributions measurements thereby determining the RBCW from images obtained with clinical microscopes. The new algorithm according to the present invention, deriving the red blood cell width, vessel diameter, glycocalyx width, and Capillary Volume Reserve directly from sequential measurements of the width of the column of red blood cells in a given blood vessel, was used for the measurements. The method analyzed the distribution of more than 1000 RBCW values in a given vessel, thereby revealing that a few percent of the RBCW measurements extend into the glycocalyx domain on the luminal endothelial membrane from which RBCs are generally excluded. Only a few seconds of RBC perfusion were required in a given microvessel to allow the analysis of the status of the glycocalyx and all microvessels in a given field of view were analyzed simultaneously. Recording of a single field of view took only seconds, and recording of multiple fields of view was accomplished within one of several minutes. As a result, accurate distributions of red blood cell width, vessel diameter, glycocalyx width, and Capillary Volume Reserve from more than 100 blood vessels were obtained.

Results

The measurements of the status of the glycocalyx were compared between subjects treated with a sublingual spray nitroglycerine and untreated control subjects. The sublingual spray nitroglycerine provides a controlled stimulus since nitroglycerine is known to cause damage to the glycocalyx. As shown in FIGS. 5A and 5B, a clear distinction between the status of the glycocalyx in treated and untreated subjects can be seen. The detection of the dynamic change of the status of the glycocalyx as performed in the present example could be detected in a matter of minutes. The status of the glycocalyx directly correlated to the RBCW (FIGS. 5A vs 5B).

The results also showed that an analysis of only 100 RBCs provided similar results.

CONCLUSIONS

These data demonstrates that the status of the glycocalyx can be performed using the methods of the present invention. Furthermore, it is shown that the method of the present invention provides a fast and accurate way to detect dynamic changes in the status of the glycocalyx.

Example 4

The present example demonstrates that by establishing the status of the glycocalyx, using the method as described in Example 2, the present invention enables the differentiation between the status of the glycocalyx in cases of cancer and healthy controls. Also the effect of treatment can be assessed as well.

Results

The measurements of the status of the glycocalyx were compared between subjects diagnosed with cancer and healthy control subjects. As shown in FIGS. 6A and 6B, a clear distinction between the status of the glycocalyx in healthy and cancer subjects can be seen. The detection of the dynamic change of the status of the glycocalyx as performed in the present example could be detected in a matter of minutes.

After treatment of the diagnosed subjects with a VEGF receptor inhibiting compound, the effect of this treatment can be visualized as shown in FIGS. 7A and 7B.

CONCLUSIONS

These data demonstrates that the status of the glycocalyx can be used to diagnose damage to the glycocalyx, in this example damage caused by cancer. Furthermore, the effect of the treatment of the cancer with specific compounds can be assessed.

Example 5

The present example demonstrates that by establishing the status of the glycocalyx, using the method as described in Example 2, the present invention enables the differentiation between the status of the glycocalyx in cases of diabetes and healthy controls. Also the effect of treatment can be assessed as well.

21 non-smoking, male patients with diabetes mellitus type 2 without overt signs of macrovascular disease, defined as a history of myocardial infarction, stroke, peripheral vascular disease or signs of macrovascular disease at physical examination, were used as the diabetes group. Thirteen normoglycemic, non-smoking, healthy male subjects served as a control group.

Results

The measurements of the status of the glycocalyx were compared between subjects diagnosed with Diabetes (without micro-albuminuria) and healthy control subjects. As shown in FIGS. 8A and 8B, a clear distinction between the status of the glycocalyx in healthy and diabetic subjects can be seen. The detection of the dynamic change of the status of the glycocalyx as performed in the present example could be detected in a matter of minutes.

After treatment of the diagnosed subjects with a glycomimetic compound, the effect of this treatment can be visualized as shown in FIGS. 9A and 9B.

CONCLUSIONS

These data demonstrates that the status of the glycocalyx can be used to diagnose damage to the glycocalyx, in this example damage caused by diabetes. Furthermore, the effect of the treatment of the diabetes with specific compounds can be assessed.

The invention claimed is:

1. A method for reconstituting the integrity of a glycocalyx, the method comprising the steps of:
    (i) assessing the status of the glycocalyx by:
        (a) determining the width of at least 10 Red Blood Cells in a microvascular blood vessel;
        (b) repeating step (a) for at least 10 microvascular blood vessels; and,
        (c) determining the median or average red blood cell width value from the determined widths, wherein the glycocalyx width equals half of the difference between the maximal red blood cell width value and the median red blood cell width value; thereby assessing the status of the glycocalyx;
    (ii) reconstituting the integrity of the glycocalyx when the assessment of the status of the glycocalyx indicates that the status of the glycocalyx is compromised.

2. The method according to claim 1, additionally comprising the step of:
    (d) determining the Capillary Volume Reserve from the size distribution of the red blood cell width measurements, wherein the Capillary Volume Reserve is the square of the maximum red blood cell width divided by the square of the mean red blood cell width.

3. The method according to claim 1, wherein the maximal red blood cell width value comprises the P99 value of the red blood cell width distribution; or RBCWmax.

4. The method according to claim 1, wherein the median red blood cell width value comprises the P50 value of the red blood cell width distribution; or RBCWmedian.

5. A method for identifying compounds, cardiovascular risk factors, or lifestyle factors modulating the status of the glycocalyx, the method comprising:
    determining a baseline status of the glycocalyx in a subject via a method comprising:
        (a) determining the width of at least 10 Red Blood Cells in a microvascular blood vessel;

(b) repeating step (a) for at least 10 microvascular blood vessels;
(c) determining the median or average red blood cell width value from the determined widths, wherein the glycocalyx width equals half of the difference between the maximal red blood cell width value and the median red blood cell width value; thereby determining the baseline status of the glycocalyx;

administering to the subject a compound of interest or altering a cardiovascular risk factor or a lifestyle factor in the subject;

determining, after the administration or alteration, an experimental status of the glycocalyx in the subject via a method comprising:
(a) determining the width of at least 10 Red Blood Cells in a microvascular blood vessel in the presence and absence of a compound of interest, cardiovascular risk factor, or lifestyle factor;
(b) repeating step (a) for at least 10 microvascular blood vessels;
(c) determining the median or average red blood cell width value from the determined widths, wherein the glycocalyx width equals half of the difference between the maximal red blood cell width value and the median red blood cell width value; thereby determining the baseline status of the glycocalyx;

wherein a difference in the baseline status of the glycocalyx and the experimental status of the glycocalyx identifies said compound, cardiovascular risk factor, or lifestyle factor as modulating the status of the glycocalyx.

6. A computer comprising a processor, memory, and a computer program, wherein the computer program directs the processor to:
(a) read red blood cell width distribution data; and
(b) determine the width of at least 10 Red Blood Cells in a microvascular blood vessel;
(c) repeat step (b) for at least 10 microvascular blood vessels; and,
(d) determine the median or average red blood cell width value from the determined widths,
wherein the glycocalyx width equals half of the difference between the maximal red blood cell width value and the median red blood cell width value.

* * * * *

UNITED STATES PATENT AND TRADEMARK OFFICE
CERTIFICATE OF CORRECTION

PATENT NO. : 8,759,095 B2  
APPLICATION NO. : 12/734876  
DATED : June 24, 2014  
INVENTOR(S) : Hans Vink and Erik Sjoerd Gerard Stroes Page 1 of 1

It is certified that error appears in the above-identified patent and that said Letters Patent is hereby corrected as shown below:

On the title page:
In ITEM (30) Foreign Application Priority Data
change "07122043" to --07122043.8--

Signed and Sealed this
Twenty-second Day of December, 2015

Michelle K. Lee
*Director of the United States Patent and Trademark Office*